(12) United States Patent
Bruszewski et al.

(10) Patent No.: US 8,333,800 B2
(45) Date of Patent: Dec. 18, 2012

(54) MOBILE EXTERNAL COUPLING WITH INTERNAL SEALING CUFF FOR BRANCH VESSEL CONNECTION

(75) Inventors: Walter Bruszewski, Santa Rosa, CA (US); Heath Muzslay, Petaluma, CA (US); Emilie Johnson, Cotati, CA (US); Kevin Boyle, Santa Rosa, CA (US); Mohammed Iftekhar, Santa Rosa, CA (US); Samuel Robaina, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 92 days.

(21) Appl. No.: 12/770,536

(22) Filed: Apr. 29, 2010

(65) Prior Publication Data

US 2011/0270378 A1    Nov. 3, 2011

(51) Int. Cl.
   *A61F 2/06* (2006.01)
(52) U.S. Cl. ............... 623/1.35; 623/1.13; 623/1.15
(58) Field of Classification Search ........ 623/1.15, 623/1.13, 1.35; *A61F 2/06*
   See application file for complete search history.

(56) References Cited

U.S. PATENT DOCUMENTS

| | | | |
|---|---|---|---|
| 3,692,618 A | 9/1972 | Dorschner et al. | |
| 3,802,817 A | 4/1974 | Matsuki et al. | |
| 4,340,563 A | 7/1982 | Appel et al. | |
| 5,387,235 A | 2/1995 | Chuter | |
| 5,456,713 A | 10/1995 | Chuter | |
| 5,693,084 A | 12/1997 | Chuter | |
| 5,709,713 A | 1/1998 | Evans et al. | |
| 5,720,776 A | 2/1998 | Chuter et al. | |
| 5,755,772 A | 5/1998 | Evans et al. | |
| 5,800,514 A | 9/1998 | Nunez et al. | |
| 5,984,955 A * | 11/1999 | Wisselink | 623/1.35 |
| 6,248,097 B1 | 6/2001 | Beitz et al. | |
| 6,465,073 B1 | 10/2002 | Morman et al. | |
| 6,565,597 B1 | 5/2003 | Fearnot et al. | |
| 6,994,724 B2 | 2/2006 | Schmitt | |
| 7,189,257 B2 | 3/2007 | Schmitt et al. | |

(Continued)

FOREIGN PATENT DOCUMENTS

EP   0556749   2/1993

(Continued)

OTHER PUBLICATIONS

U.S. Appl. No. 12/425,616, filed Apr. 17, 2009, Bruszewski et al. U.S. Appl. No. 12/425,628, filed Apr. 17, 2009, Bruszewski et al.

*Primary Examiner* — Christopher D Koharski
*Assistant Examiner* — Jason-Dennis Stewart

(57) ABSTRACT

An endovascular prosthesis includes a tubular body and a mobile external coupling. The tubular body includes a graft material and stents coupled thereto, a forms a lumen therethrough. The mobile external coupling extends outwardly from the tubular body. The mobile external coupling includes a graft material and is generally frustoconically shaped. The mobile external coupling includes a base coupled to the tubular body, a top spaced from the tubular body, and a coupling lumen disposed between the base and the top, wherein the coupling lumen is in flow communication with the body lumen. A cylindrical sealing cuff of graft material is attached to and extends from the top of the mobile external coupling towards the tubular body within the coupling lumen. The sealing cuff is configured to contact a portion of a branch vessel prosthesis and thereby provides an elongated interference seal between the branch vessel prosthesis and the mobile external coupling.

12 Claims, 16 Drawing Sheets

U.S. PATENT DOCUMENTS

| | | |
|---|---|---|
| 7,264,632 B2 | 9/2007 | Wright et al. |
| 2003/0199967 A1 | 10/2003 | Hartley |
| 2005/0143806 A1 | 6/2005 | Phillips |
| 2006/0229561 A1 | 10/2006 | Huszar |
| 2006/0276883 A1* | 12/2006 | Greenberg et al. .......... 623/1.31 |
| 2007/0244542 A1 | 10/2007 | Greenan |
| 2008/0114442 A1 | 5/2008 | Mitchell et al. |
| 2008/0262590 A1 | 10/2008 | Murray |
| 2009/0276027 A1 | 11/2009 | Glynn |
| 2010/0114294 A1* | 5/2010 | Rasmussen et al. ......... 623/1.15 |

FOREIGN PATENT DOCUMENTS

| | | |
|---|---|---|
| EP | 1201212 | 5/2002 |
| WO | WO93/16669 | 9/1993 |
| WO | WO99/13808 | 3/1999 |
| WO | WO2005/034810 | 4/2005 |
| WO | WO2005/037160 | 4/2005 |
| WO | WO2006/113501 | 10/2006 |
| WO | WO2010/024879 | 3/2010 |

* cited by examiner

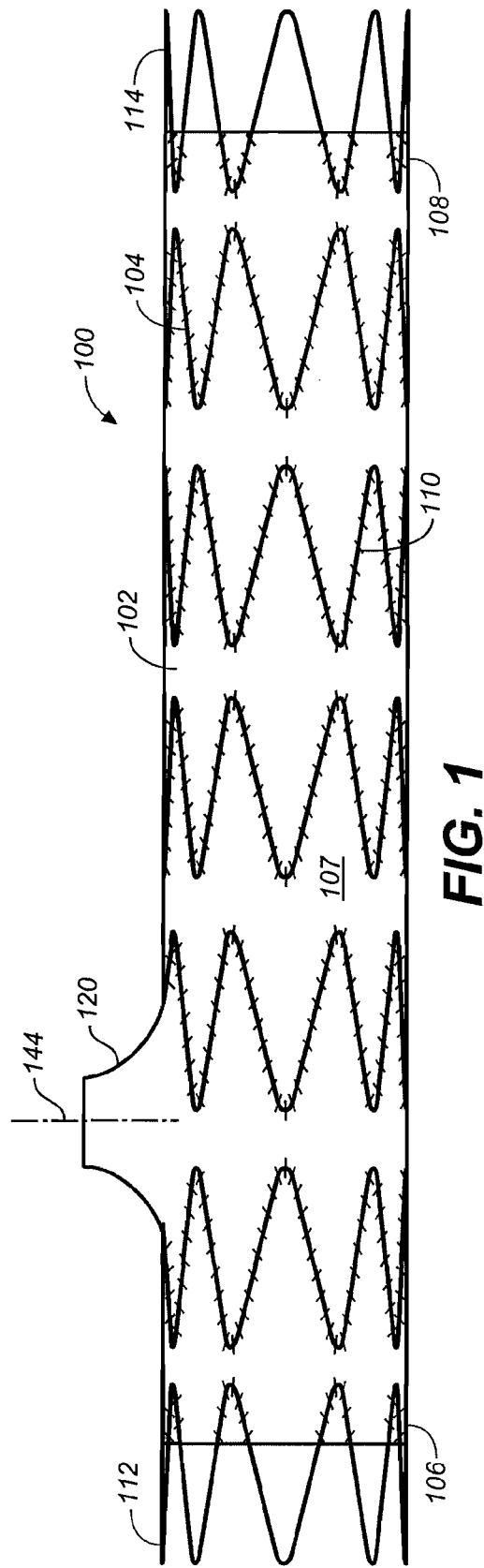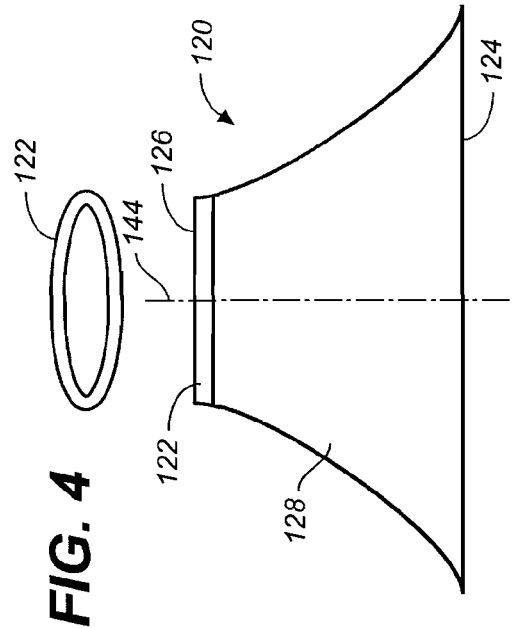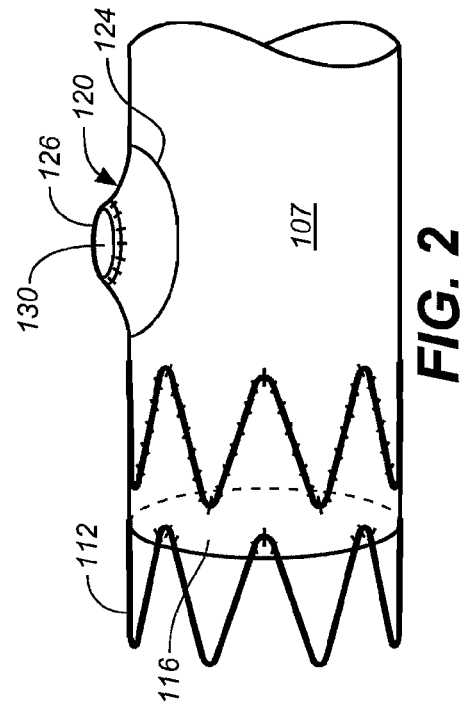

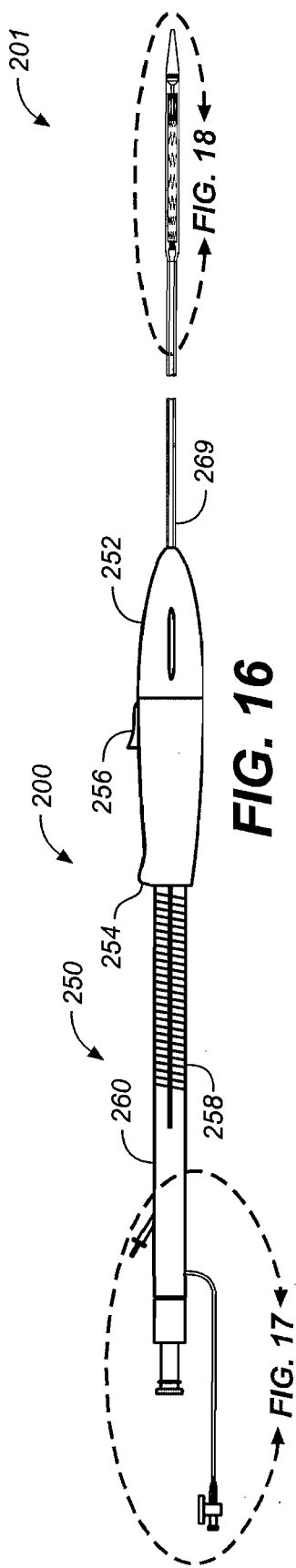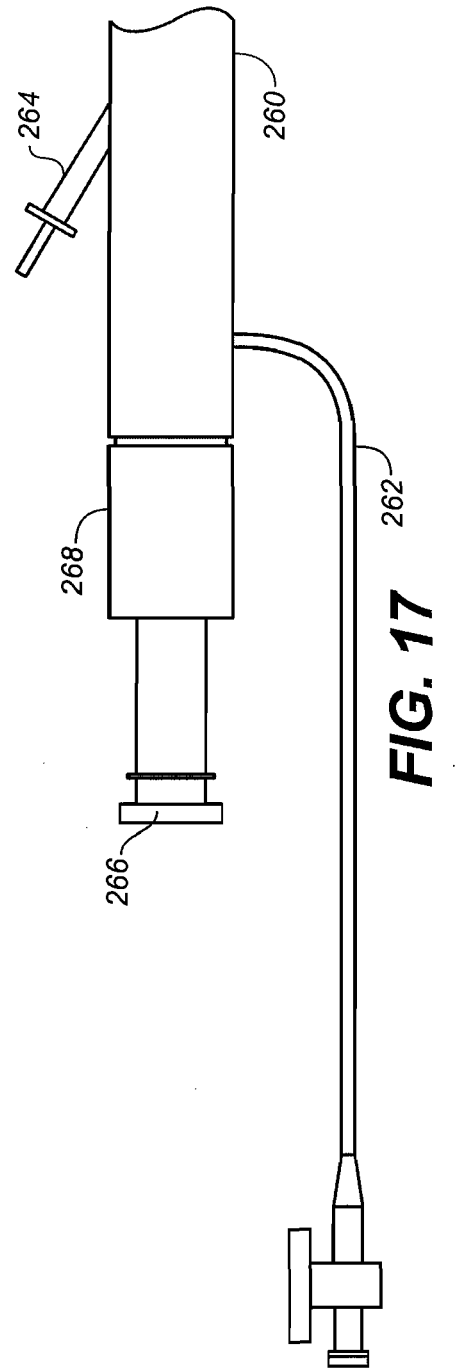

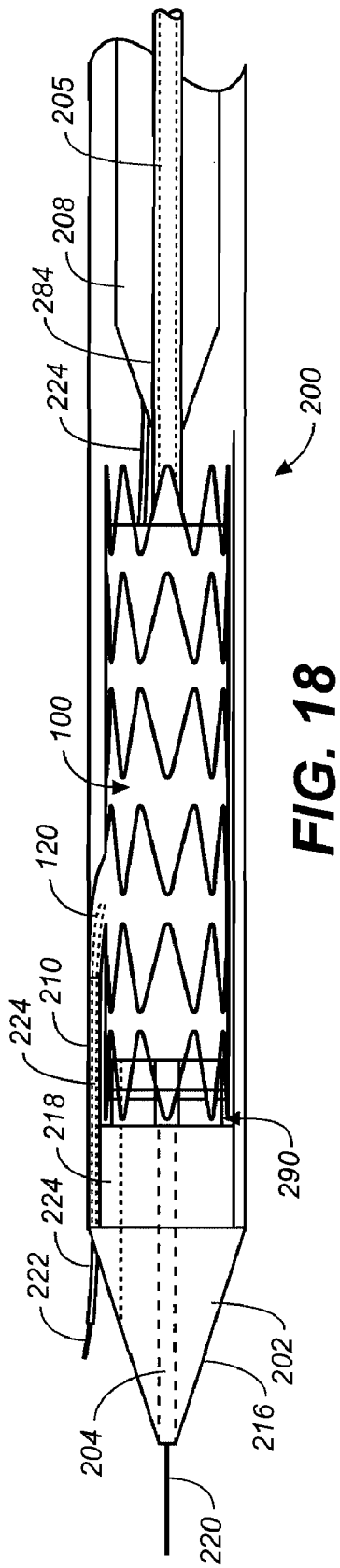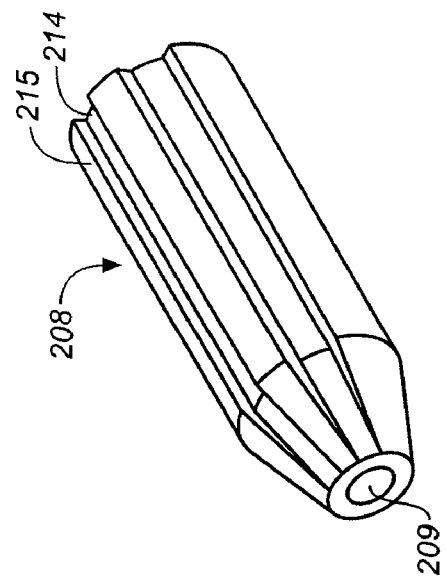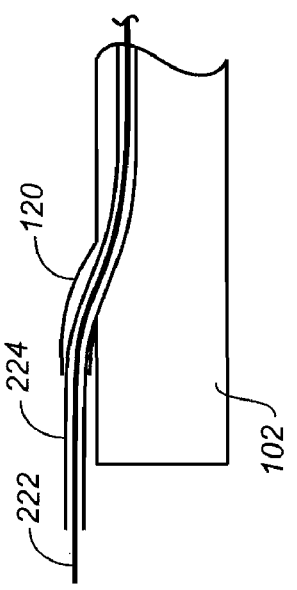

US 8,333,800 B2

MOBILE EXTERNAL COUPLING WITH INTERNAL SEALING CUFF FOR BRANCH VESSEL CONNECTION

FIELD OF THE INVENTION

This invention relates generally to endoluminal medical devices and procedures, and more particularly to an endoluminal prosthesis or graft having a mobile external coupling for connecting a main graft to a branch vessel graft.

BACKGROUND

Aneurysms and/or dissections may occur in blood vessels, and most typically occur in the aorta and peripheral arteries. Depending on the region of the aorta involved, the aneurysm may extend into areas having vessel bifurcations or segments of the aorta from which smaller "branch" arteries extend. Various types of aortic aneurysms may be classified on the basis of the region of aneurysmal involvement. For example, thoracic aortic aneurysms include aneurysms present in the ascending thoracic aorta, the aortic arch, and branch arteries that emanate therefrom, such as subclavian arteries, and also include aneurysms present in the descending thoracic aorta and branch arteries that emanate therefrom, such as thoracic intercostal arteries and/or the suprarenal abdominal aorta and branch arteries that emanate therefrom, which could include renal, superior mesenteric, celiac and/or intercostal arteries. Lastly, abdominal aortic aneurysms include aneurysms present in the aorta below the diaphragm, e.g., pararenal aorta and the branch arteries that emanate therefrom, such as the renal arteries.

The thoracic aorta has numerous arterial branches. The arch of the aorta has three major branches extending therefrom, all of which usually arise from the convex upper surface of the arch and ascend through the superior thoracic aperture. The brachiocephalic artery originates anterior to the trachea. The brachiocephalic artery divides into two branches, the right subclavian artery (which supplies blood to the right arm) and the right common carotid artery (which supplies blood to the right side of the head and neck). The left common carotid artery arises from the arch of the aorta just to the left of the origin of the brachiocephalic artery. The left common carotid artery supplies blood to the left side of the head and neck. The third branch arising from the aortic arch, the left subclavian artery, originates behind and just to the left of the origin of the left common carotid artery and supplies blood to the left arm.

For patients with thoracic aneurysms of the aortic arch, surgery to replace the aorta may be performed where the aorta is replaced with a fabric substitute in an operation that uses a heart-lung machine. In such a case, the aneurysmal portion of the aorta is removed or opened and a substitute lumen is sewn across the aneurysmal portion to span it. Such surgery is highly invasive, requires an extended recovery period and, therefore, cannot be performed on individuals in fragile health or with other contraindicative factors.

Alternatively, the aneurysmal region of the aorta can be bypassed by use of am endoluminally delivered tubular exclusion device, e.g., by a stent-graft placed inside the vessel spanning the aneurysmal portion of the vessel, to seal off the aneurysmal portion from further exposure to blood flowing through the aorta. A stent-graft can be implanted without a chest incision, using specialized catheters that are introduced through arteries, usually through incisions in the groin region of the patient. The use of stent-grafts to internally bypass, within the aorta or flow lumen, the aneurysmal site, is also not without challenges. In particular, where a stent-graft is used at a thoracic location, care must be taken so that critical branch arteries are not covered or occluded by the stent-graft yet the stent-graft must seal against the aorta wall and provide a flow conduit for blood to flow past the aneurysmal site. Where the aneurysm is located immediately adjacent to the branch arteries, there is a need to deploy the stent-graft in a location which partially or fully extends across the location of the origin of the branch arteries from the aorta to ensure sealing of the stent-graft to the artery wall.

To accommodate side branches, main vessel stent-grafts having a fenestration or opening in a side wall thereof may be utilized. The main vessel stent graft is positioned to align its fenestration with the ostium of the branch vessel. In use, a proximal end of the stent-graft, having one or more side openings, is prepositioned and securely anchored in place so that its fenestrations or openings are oriented when deployed to avoid blocking or restricting blood flow into the side branches. Fenestrations by themselves do not form a tight seal or include discrete conduit(s) through which blood can be channeled into the adjacent side branch artery. As a result, blood leakage is prone to occur into the space between the outer surface of the main aortic stent graft and the surrounding aortic wall between the edge of the graft material surrounding the fenestrations and the adjacent vessel wall. Similar blood leakage can result from post-implantation migration or movement of the stent-graft causing misalignment between the fenestration(s) and the branch artery(ies), which may also result in impaired flow into the branch artery(ies).

In some cases, the main vessel stent graft is supplemented by another stent-graft, often referred to as a branch stent-graft. The branch graft is deployed through the fenestration into the branch vessel to provide a conduit for blood flow into the branch vessel. The branch stent-graft is preferably sealingly connected to the main graft in situ to prevent undesired leakage between it and the main stent-graft. This connection between the branch graft and main graft may be difficult to create effectively in situ and is a site for potential leakage.

In some instances, branch graft extensions (stent-grafts) are incorporated into the main stent-graft. Such branch graft extensions are folded or collapsed against the main stent-graft for delivery and require complicated procedures, requiring multiple sleeves and guide wires, to direct the branch extension into the branch vessel and subsequently expand. Further, in some instances, such branch stent-grafts tend to return to their folded or collapsed configuration, and thus do not provide an unobstructed flow path to the branch vessel.

Thus, there remains a need in the art for improvements in stent graft structures for directing flow from a main vessel, such as the aorta, into branch vessels emanating therefrom, such as branch vessels of the aortic arch.

SUMMARY OF THE INVENTION

Embodiments hereof relate to an endovascular prosthesis includes a tubular body and a mobile external coupling. The tubular body includes a graft material and stents coupled thereto, and forms a lumen therethrough. The mobile external coupling extends outwardly from the tubular body. The mobile external coupling includes graft material and is generally frustoconically shaped. The mobile external coupling includes a base coupled to the tubular body, a top spaced from the tubular body in its extended configuration, and a coupling lumen disposed between the base and the top, wherein the coupling lumen is in flow communication with the body lumen. A cylindrical sealing cuff formed from a graft material is attached to and extends from the top of the mobile external coupling towards the tubular body. The sealing cuff is configured to contact a portion of the branch vessel prosthesis and thereby provides an elongated interference seal between the branch vessel prosthesis and the mobile external coupling.

BRIEF DESCRIPTION OF DRAWINGS

FIG. 1 is a schematic side view of an endoluminal stent-graft illustrating an embodiment hereof.

FIG. 2 is a schematic close up illustration of a portion of the stent-graft of FIG. 1.

FIG. 3 is a schematic illustration of the mobile external coupling of the stent-graft of FIG. 1.

FIG. 4 is a schematic illustration of a stent ring disposed at the top of the mobile external coupling of the stent-graft of FIG. 1.

FIG. 16 is a schematic illustration of a stent-graft delivery device.

FIG. 17 is a schematic illustration of a proximal portion of the stent-graft delivery device of FIG. 16.

FIG. 18 is a schematic illustration of a distal portion of the stent-graft delivery device of FIG. 16 with a stent-graft disposed therein.

FIG. 19 is a schematic illustration of a stent graft with a side tube for the second guide wire extending through a lumen of the tubular body of the stent-graft and through a lumen of the mobile external coupling.

FIG. 20 is a schematic illustration of a stent stop including grooves for the side tube.

DETAILED DESCRIPTION

Figure 5A:
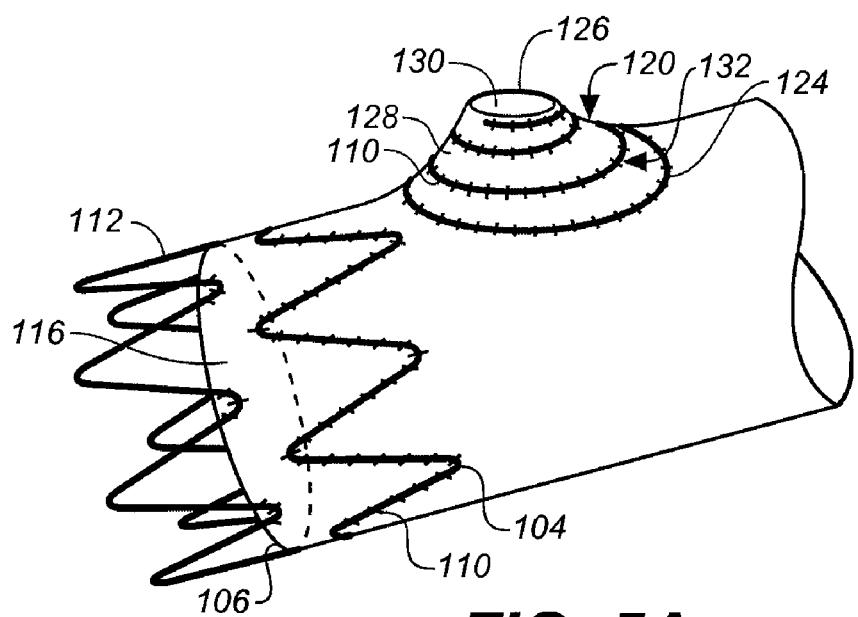
FIG. 5A is a schematic illustration of the mobile external coupling of the stent-graft having a coupling deployment mechanism coupled thereto.

Specific embodiments are now described with reference to the figures, wherein like reference numbers indicate identical or functionally similar elements. Unless otherwise indicated, for the delivery system the terms "distal" and "proximal" are used in the following description with respect to a position or direction relative to the treating clinician. "Distal" and "distally" are positions distant from or in a direction away from the clinician, and "proximal" and "proximally" are positions near or in a direction toward the clinician. For the stent graft device "proximal" is the portion nearer the heart by way of blood flow path while "distal" is the portion of the stent graft further from the heart by way of blood flow path.

With reference to FIGS. 1-4, a stent-graft 100 is configured for placement in a vessel such as the aorta. Stent-graft 100 includes graft material 102 coupled to circumferential stents 104. Graft material 102 may be coupled to circumferential stents 104 using stitching 110 or other means known to those of skill in the art. In the embodiment shown in FIGS. 1-2 circumferential stents 104 are coupled to an outside surface of graft material 102. However, circumferential stents 104 may alternatively be coupled to an inside surface of graft material 102. Graft material 102 may be any suitable graft material, for example and not limited to, woven polyester, DACRON® material, expanded polytetrafluoroethylene, polyurethane, silicone, or other suitable materials. Circumferential stents 104 may be any conventional stent material or configuration. As shown, circumferential stents 104 are preferably made from a shape memory material, such as thermally treated stainless steel or nickel-titanium alloy (nitinol), and are formed into a zig-zag configuration. Stent-graft 100 includes a proximal end 106, a distal end 108, and a body 107 therebetween. Proximal stent 112 and distal stent 114 may extend outside of the graft material 102, as shown, and may also be generally described as anchor stents or crown stents in the art. Body 107 has a lumen 116 therethrough. Stent-graft 100 further includes a mobile external coupling 120, described in detail below. Except for the mobile external coupling 120, stent-graft 100 may be similar to the Medtronic, Inc.'s VALIANT® thoracic stent-graft, or other known stent-grafts.

Mobile external coupling 120 is disposed on an outside surface of stent-graft 100 corresponding to an opening in graft material 102. Mobile external coupling 120 is generally frustoconically shaped. Mobile external coupling 120 includes graft material 128 having a base 124 and a top 126. Graft material 128 is preferably the same type of graft material as graft material 102 of the body 107 and is preferably a continuation of graft material 102, although graft material 128 can be a separate piece of graft material attached to graft material 102. As shown in FIGS. 3 and 4, a wire shaped as a circle or ring 122 may be disposed at top 126 and may be coupled to graft material 128 by creating a blanket stitch which captures the edge of the graft material 128 and the ring 122 with suture material. The suture describes a helical path as it progresses around the ring 122. The density of the stitch is such that it essentially covers the ring with suture. Although mobile external coupling 120 is described as generally frustoconical in shape, base 124 is preferably generally elliptical rather than circular. Base 124 may have, for example and not by way of limitation, a long axis of approximately 20-30 mm and a short axis of approximately 15-20 mm. Further, the height of mobile external coupling 120 may be approximately 10-15 mm. Further, the diameter of the top 126 of mobile external coupling may be approximately 6-9 mm if it is to be used at the junction of the aorta and left common carotid artery or the junction of the aorta and left subclavian artery. If the mobile external coupling 120 is to be used at the junction of the aorta and the brachiocephalic artery, the diameter of the top 126 may be approximately 8-12 mm.

Figure 5B:
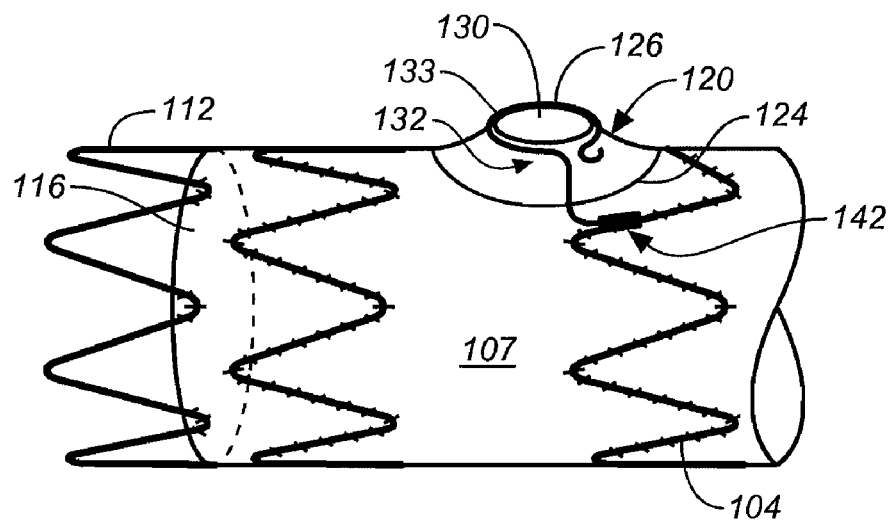
FIG. 5B is a schematic illustration of the mobile external coupling of the stent-graft having a coupling deployment mechanism coupled thereto.

Referring to FIGS. 5A-5B, a coupling deployment device 132 may be coupled to mobile external coupling 120 for elevating top 126 of mobile external coupling 120 into the ostium of the target branch vessel during deployment and ensuring that mobile external coupling 120 fully everts into the ostium. In an embodiment, coupling deployment device 132 may be a shape memory helical stent coupled to graft material 128 as shown in FIG. 5A. The helical stent is configured to create the frustoconically shaped outline such that bottom 124 has a larger diameter than top 124, as described in U.S. patent application Ser. No. 12/425,628, filed Apr. 17, 2009, herein incorporated by reference in its entirety. In another embodiment, coupling deployment device 132 may be a shape set wire coupled to a circumferential stent 104 of stent grail 100 via a crimp 142 as shown in FIG. 5B. The shape set wire has one or more spring arm portions that extend generally longitudinally along mobile external coupling 120 such that mobile external coupling 120 self-extend away from body 107 when mobile external coupling 120 is released from its delivery system, as described in U.S. patent application Ser. No. 12/770,566, filed, Apr. 29, 2010, herein incorporated by reference in its entirety. In yet another embodiment, in order to deploy mobile external coupling 120 into the ostium of the target branch vessel, graft material 128 may be a woven fabric with warp yarn which run generally parallel to a longitudinal axis of the mobile external coupling including a shape memory material as described in U.S. patent application Ser. No. 12/425,616, filed Apr. 17, 2009, herein incorporated by reference in its entirety.

Mobile external coupling 120 allows for significant flexibility in aligning stent-graft 100 with a branch vessel because the top of the mobile external coupling 120 when deployed can move longitudinally relative to the longitudinal axis of the body 107. This mobility is due to the shape of mobile external coupling 120 and can be further improved by utilizing some excess graft material 128 when forming mobile external coupling 120. Thus, if stent-graft 100 is not perfectly aligned with a branch vessel, the top 126 of mobile external coupling 120 can move or shift to cause top to extend into the branch vessel. Further, due to the energy stored in coupling deployment device 132 while in the delivery or collapsed configuration in its delivery system, mobile external coupling 120 pops out from body 107 of stent-graft 100 when released from a sleeve of the delivery system during delivery and deployment at the target site. Thus, when mobile external coupling 120 is released from its delivery configuration, as explained in more detail below, mobile external coupling 120 will self expand to extend away from body 107. This prevents bunching, kinking or collapse of the mobile external coupling 120 when released from the delivery system.

Figure 6:
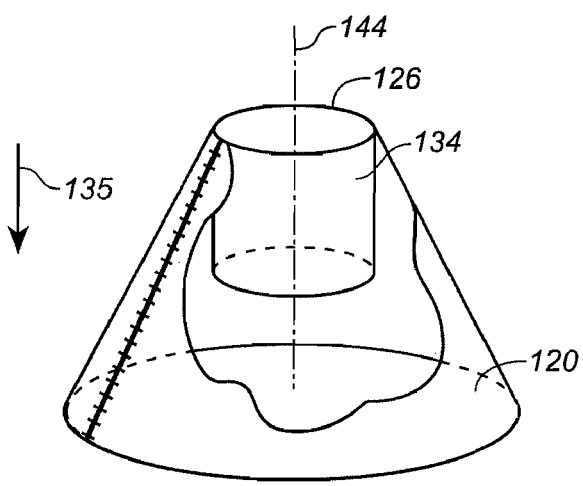
FIG. 6 is a schematic illustration of the mobile external coupling having a portion cut-away to illustrate an internal sealing cuff.
Figure 7:
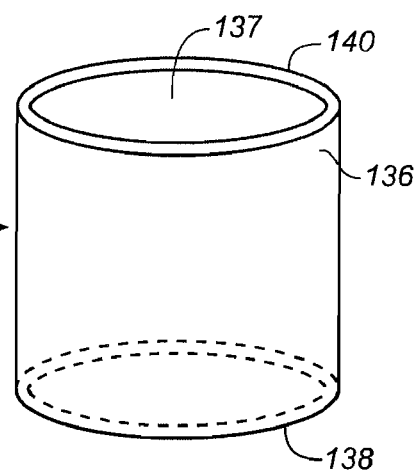
FIG. 7 is a schematic illustration of the internal sealing cuff of FIG. 6 removed from the mobile external coupling.
Figure 8:
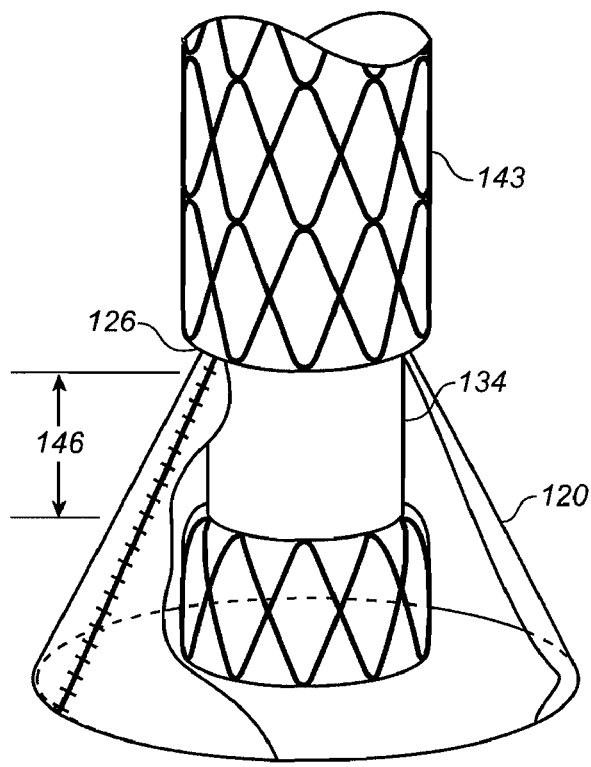
FIG. 8 is a schematic illustration of the mobile external coupling having a portion cut-away to illustrate the internal sealing cuff having a branch vessel conduit deployed therein.

As will be explained in more detail herein, a branch vessel prosthesis or conduit is delivered and deployed through mobile external coupling 120. After implantation, pulsatile expansion and/or other movement of the branch vessel may occur during the cardiac cycle. If the branch vessel prosthesis is balloon-expandable, such movement of the branch vessel may eventually degrade the seal between mobile external coupling 120 and a branch vessel prosthesis 143 due to plastic deformation of the material of branch vessel prosthesis 143. Referring now to FIGS. 6-8, an internal sealing cuff 134 is attached to the top 126 of mobile external coupling 120 for producing an elongated interference seal or longitudinal contact zone 146 (shown in FIG. 8) between branch vessel prosthesis 143 (shown in FIG. 8) and mobile external coupling 120. FIG. 6 is a schematic illustration of mobile external coupling 120 having a portion cut-away to reveal internal sealing cuff 134 extending therein, and FIG. 7 is a schematic illustration of internal sealing cuff 134 removed from mobile external coupling 120. FIG. 8 is a schematic illustration of mobile external coupling 120 including internal sealing cuff 134 with a branch vessel prosthesis 143 deployed therein. Regardless whether branch vessel prosthesis 143 is balloon-expandable or self-expanding, internal sealing cuff 134 enhances sealing between branch vessel prosthesis 143 and mobile external coupling 120 due to the increased amount of contact zone 146.

Internal sealing cuff 134 is generally cylindrically shaped and extends proximally or inwardly from the top 126 of mobile external coupling 120 in a direction towards body 107 indicated by directional arrow 135, such that sealing cuff 134 is internal to mobile external coupling 120. Internal sealing cuff 134 and mobile external coupling 120 share the same longitudinal axis 144, and internal sealing cuff 134 includes a lumen 137 extending therethrough which is in fluid communication with coupling lumen 130 of mobile external coupling 120. Internal sealing cuff 134 may be formed of a graft material 136 having a base 138 and a top 140. Graft material 136 may be any suitable graft material, for example and not limited to, woven polyester, DACRON® material, expanded polytetrafluoroethylene (PET), polyurethane, silicone, or other suitable materials. In one embodiment, graft material 136 is a pliable cloth material suitable that can withstand the expansion or inflation force of the branch vessel prosthesis without crumpling or failing. If branch vessel prosthesis 143 is balloon-expandable, a pliable cloth graft material is unlikely to create plastic deformation of branch vessel prosthesis 143. In an example, and not by way of limitation, graft material 136 may be a seamless woven tube of PET cloth. Top 140 of internal sealing cuff 134 is attached to top 126 of mobile external coupling 120 using any suitable mechanical method such as sewing or adhesive. For example, the top edge of graft material 128 of mobile external coupling 120 and the top edge of graft material 136 of internal sealing cuff may be approximated and held together by a blanket stitch. If mobile external coupling 120 includes ring 122 (see FIGS. 3-4) disposed at the top thereof, internal sealing cuff 134 may be attached to the mobile external coupling 120 by placing the edge of the graft material 136 of internal sealing cuff 134 adjacent the edge of graft material 128 of mobile external coupling and by creating a blanket stitch which captures the edges of the graft material 128, graft material 136, and the ring 122 with suture material. The suture describes a helical path as it progresses around the ring 122. The density of the stitch is such that it essentially covers the ring with suture material.

The length of internal sealing cuff 134 creates the length or amount of longitudinal contact zone 146 between branch vessel prosthesis 143 and mobile external coupling 120. In one example, internal sealing cuff 134 may be approximately 1 cm in length. When branch vessel prosthesis 143 is deployed within mobile external coupling 120, interference seal 146 may extend all or part of the length of internal sealing cuff 134. The diameter of internal sealing cuff 134 is preferably smaller than the deployed diameter of branch vessel prosthesis 143. In one embodiment, the diameter of internal sealing cuff 134 may be up to approximately 30% smaller than the deployed diameter of branch vessel prosthesis 143. For example, if mobile external coupling 120 is to be used at the junction of the aorta and left common carotid artery or the junction of the aorta and left subclavian artery in which a prosthesis used in the branch vessel has a deployed diameter between 6-9 mm, the diameter of internal sealing cuff 134 may be approximately 4-6 mm. If the mobile external coupling 120 is to be used at the junction of the aorta and the brachiocephalic artery in which a prosthesis used in the branch vessel has a deployed diameter between 8-12 mm, the diameter of internal sealing cuff 134 may be approximately 5.5-8.5 mm.

Figure 9:
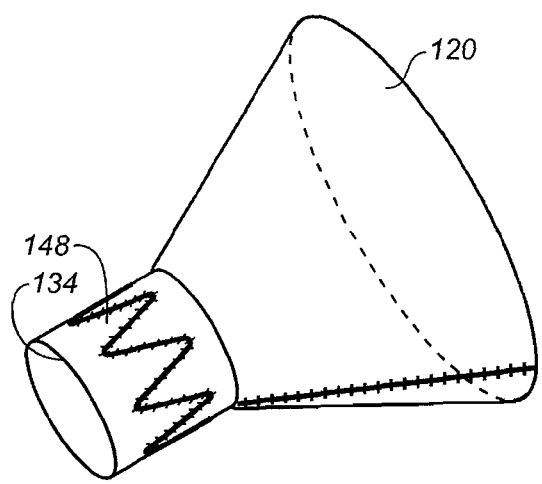
FIG. 9 is an illustration of a mobile external coupling with an internal sealing cuff, wherein the internal sealing cuff includes a circumferential stent.
Figure 10:
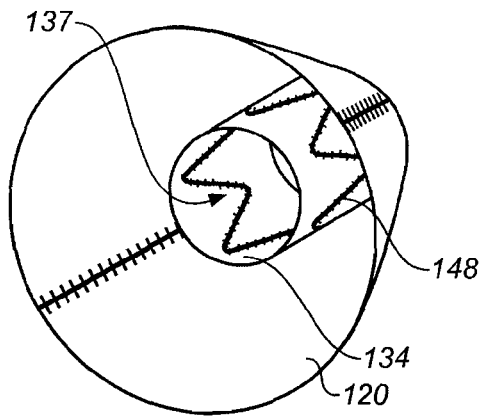
FIGS. 10-12 are different views of the mobile external coupling of FIG. 9 with an internal sealing cuff having a circumferential stent.
Figure 11:
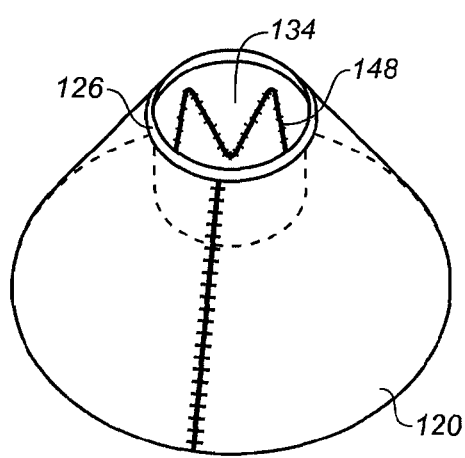
Figure 12:
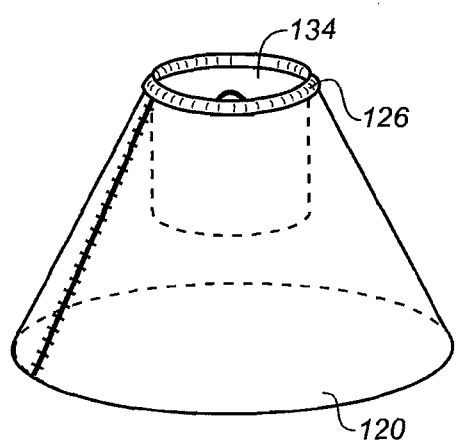
Figure 13:
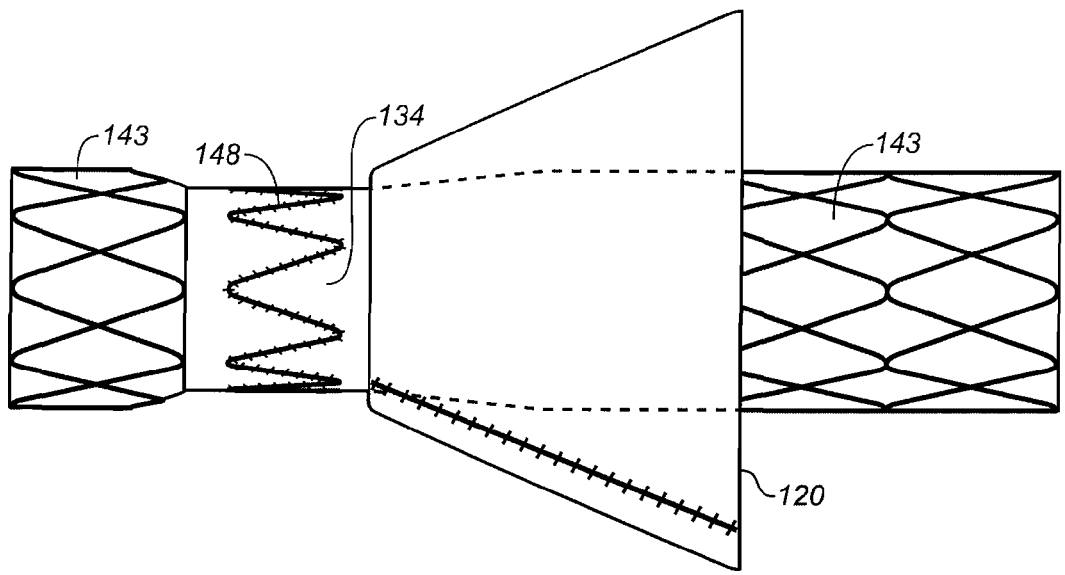
FIGS. 13-14 are views of the mobile external coupling of FIG. 9 with an internal sealing cuff having a circumferential stent and showing a branch vessel conduit deployed in the in the mobile external coupling.
Figure 14:
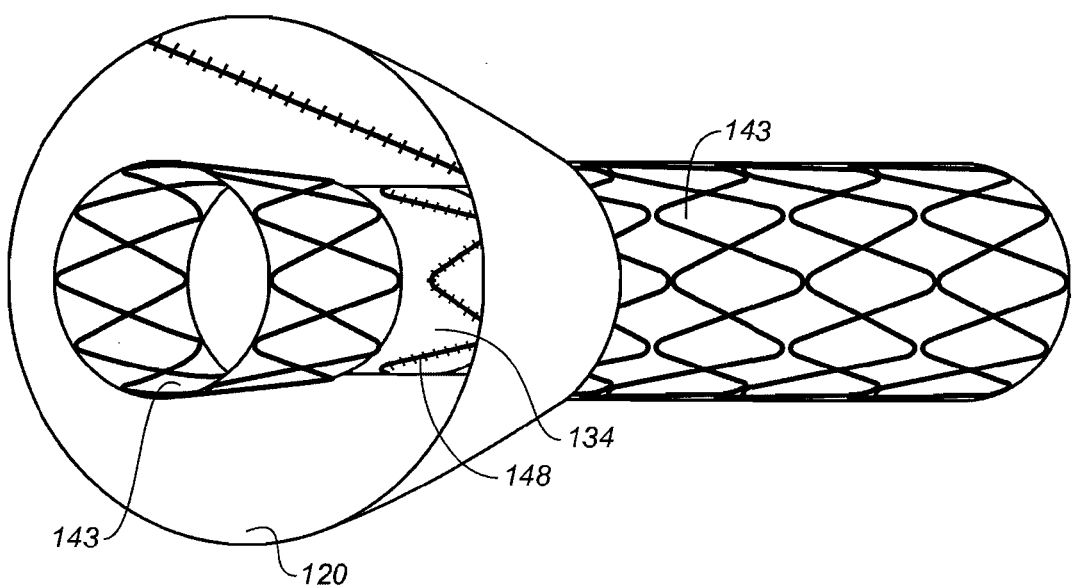

In an embodiment depicted in FIGS. 9-14, internal sealing cuff 134 may be reinforced or supported with a circumferential stent 148 coupled thereto. Stent 148 imparts longitudinal integrity to internal sealing cuff 134 to properly orient the cuff within mobile external coupling 120 and further prevent collapse of the cuff into a narrow band and/or prevent the cuff from balling or rolling up. Graft material 136 of internal sealing cuff 134 may be coupled to circumferential stent 148 using stitching or other means known to those of skill in the art, and may stent 148 be coupled to an outside or inside surface of graft material 136. Circumferential stent 148 may be any conventional stent material or configuration. As shown, circumferential stent 148 may made from a shape memory material, such as thermally treated stainless steel or nickel-titanium alloy (nitinol), and are formed into a zig-zag or sinusoidal configuration. In another embodiment, circumferential stent 148 may be formed from a plastically deformable material. FIG. 9 shows mobile external coupling 120 pulled distally to better see internal sealing cuff 134 with stent 148. FIGS. 13 and 14 show branch vessel prosthesis 143 deployed within internal sealing cuff 134, with FIG. 13 showing mobile external coupling 120 pulled distally to better see internal sealing cuff 134.

In an embodiment, circumferential stent 148 may be undersized with respect to internal sealing cuff 134 to provide a more effective seal between the cuff and branch vessel prosthesis 143. For example, if the diameter of internal sealing cuff 134 is approximately 8 mm, undersized circumferential stent 148 may have a shape memory diameter of approximately 6 mm, or 20% less than the diameter of internal sealing cuff 134. Deployment of branch vessel prosthesis 143 into internal sealing cuff 134 results in expansion of prosthesis 143 to the limiting diameter of internal sealing cuff 134. Thus, even if movement of branch vessel prosthesis 143 occurs after implantation, the shape memory of undersized circumferential stent 148 urges internal sealing cuff 134 to the shape memory diameter of undersized circumferential stent 148 to thereby compensate for the movement and retain the seal between internal sealing cuff 134 and branch vessel prosthesis 143. Undersized circumferential stent 148 and branch vessel prosthesis 143 are two elastic pieces exerting opposing forces onto each other. In other words, because branch prosthesis wants to expand to a larger diameter than the limiting diameter of stent 148, branch prosthesis 143 provides an outward force and stent 148 provides a counteracting inward force that that the seal is maintained between internal sealing cuff 134 and branch prosthesis 143. When a balloon expandable stent (BES) is used as a branch vessel prosthesis, the elastic interference interaction described may also exist, but only to the extent that elastic rebound of the BES is minimal.

Figure 15:
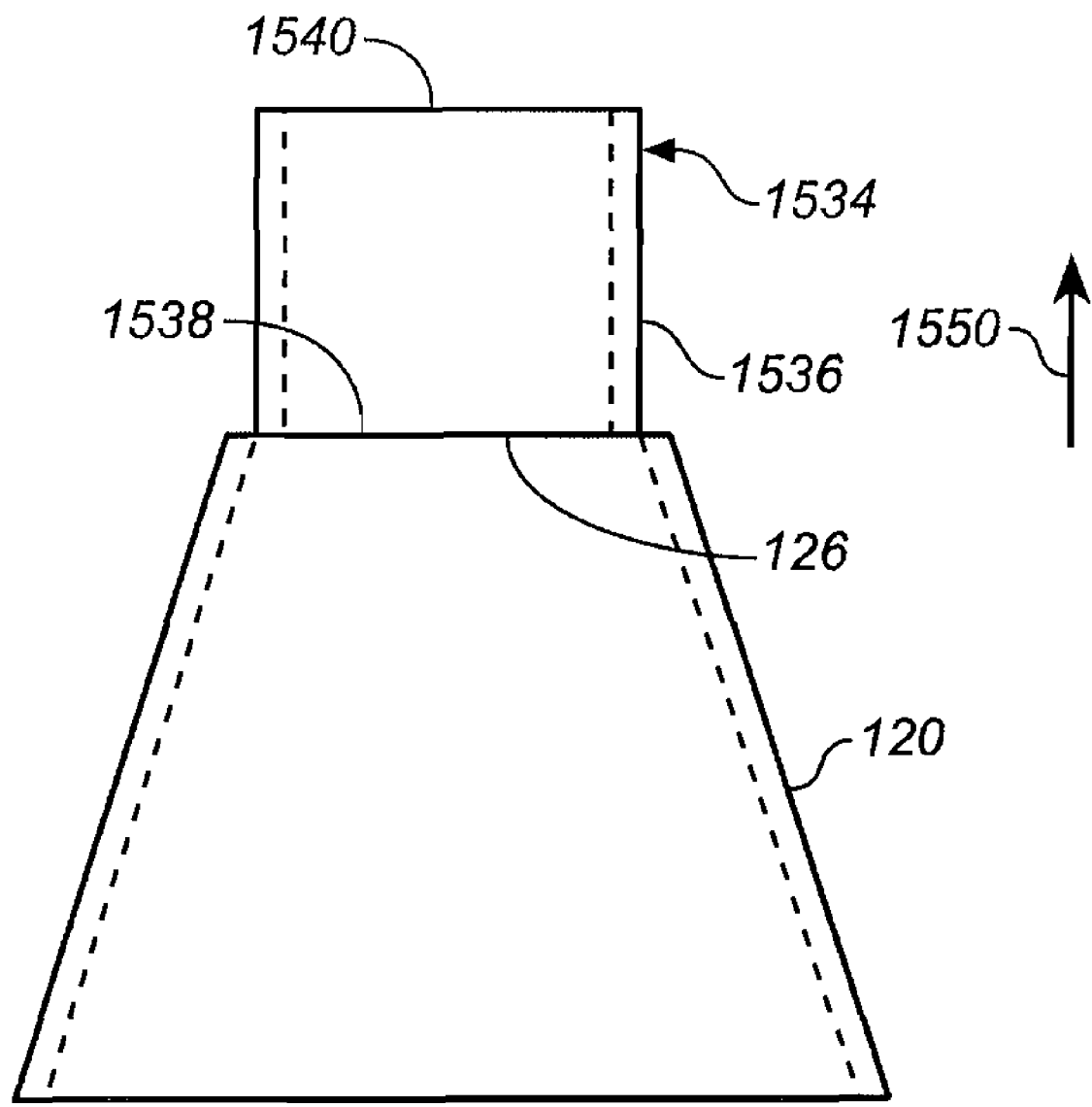
FIG. 15 is an illustration of an embodiment of a mobile external coupling with an external sealing cuff.

FIG. 15 illustrates another embodiment of a cuff for producing an elongated interference seal between the branch vessel prosthesis and the mobile external coupling. Particularly, an external sealing cuff 1534 is attached to the top 126 of mobile external coupling 120 for producing a seal or longitudinal contact zone between a branch vessel prosthesis (not shown in FIG. 15) and mobile external coupling 120. Similar to internal sealing cuff 134 described above, external sealing cuff 1534 is generally cylindrically shaped and includes graft material 1536 having a base 1538 and a top 1540. External sealing cuff 1534 operates in a similar manner as internal sealing cuff 134 to enhance sealing between a branch vessel prosthesis and mobile external coupling 120 due to the increased amount of the seal or contact zone. However, base 1538 of external sealing cuff 1534 is attached to the top 126 of mobile external coupling 120 and external sealing cuff 1534 extends distally or outwardly from the top 126 of mobile external coupling 120 in a direction away from the body of the main-stent graft (not shown in FIG. 15) indicated by directional arrow 1550, such that sealing cuff 1534 is external to mobile external coupling 120. As shown on FIG. 15, the diameter of external sealing cuff 1534 is preferably smaller than the deployed diameter of the branch vessel prosthesis, and in one embodiment may be up to approximately 30% smaller than the deployed diameter of the branch vessel prosthesis and top 126 of mobile external coupling 120. More particularly, the diameter of the top of frustoconically-shaped mobile external coupling 120 is approximately equal to the deployed diameter of the branch vessel prosthesis. External sealing cuff 1534 extends distally or outwardly from the top 126 of mobile external coupling 120, but has a diameter of up to approximately 30% smaller than top 126 for creating the seal or longitudinal contact zone between the branch vessel prosthesis and mobile external coupling 120.

FIGS. 16-26 show an example of a delivery system that can be used to deliver stent-graft 100 to the target location within a vessel. FIG. 16 is a schematic partial cross-sectional view of a stent-graft delivery system 200 with stent-graft 100 disposed therein. Stent-graft delivery system 200 includes a distal portion 201 and a proximal portion 250. Distal portion 201 is preferably used to load and deliver stent-graft section 100. Proximal portion 250 includes components such as those found conventionally in catheter delivery systems.

The components of the proximal portion 250 of the delivery system 100 may preferably include those shown in FIGS. 16 and 17, although additional and/or alternative components are also contemplated. In particular, proximal portion 250 of delivery system 200 includes a Touhy Borst adaptor 266, a stent capture slider 268, a side port extension 262, a side lumen access 264, a rear grip 260, a screw gear 258, an external slider 254 including a button 256, a front grip 252, and a strain relief 269. One or more hemostatic valves may be provided in front grip 106, for example, as described in U.S. Published Patent Application Publication No. 2006/0229561, commonly assigned with the present application, which is incorporated herein by reference in its entirety. The delivery system 200 as described is generally similar to the Xcelerant Delivery System, sold by Medtronic, Inc., but may be any conventional therapy delivery system, with modifications noted in detail below. Delivery system 200 is generally a single use, disposable device with the stent-graft 100 mounted on within distal end 201 of the delivery system 200.

FIG. 18 is a schematic view of the distal portion 201 of delivery system 200. Distal portion 201 includes a tapered tip 202 that is flexible and able to provide trackability in tight and tortuous vessels. Other tip shapes such as bullet-shaped tips could also be used. The tip 202 includes a lumen 204 disposed therethrough for accommodating a first guide wire 220.

Figure 22:
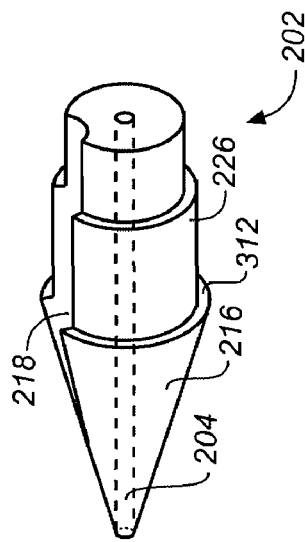
FIG. 22 is a schematic illustration of the tip of the delivery system of FIG. 16.

The tapered tip 202 includes a tapered outer surface 216 that gradually decreases in diameter in a distal direction. More particularly, tapered outer surface 216 has a first diameter at a proximal end and gradually decreases in diameter distally, i.e., in the direction away from the operator. Tapered outer surface 216 further includes a groove 218, as best seen in FIG. 22, for accommodating a second guide wire 222 within a lumen of a side tube 224. A shoulder 212 reduces the diameter of a proximal portion of tip 202 to provide a sleeve landing surface 226. Shoulder 212 is generally annular and perpendicular to a longitudinal axis of stent-graft delivery system 200.

An outer sleeve 210 of stent-graft delivery system 200 extends over the outer cylindrical surface of sleeve landing surface 226 and abuts against shoulder 212 when the stent-graft delivery system 200 is in a pre-deployment configuration, as shown in FIG. 18. Stent-graft delivery system 200 further includes a stent capture system 290 that captures and holds an end of stent-graft 100, as explained in more detail below.

Stent-graft delivery system 200 also includes an inner tube 205 that is coupled to a tip lumen 204 such that first guide wire 220 may extend the length of delivery system 200. A stent capture tube 284 of stent capture system 290 surrounds inner tube 205, as explained in more detail below. A stop 208 is located at a distal end of stent-graft 100 when stent-graft 100 is loaded onto the delivery system 200. Stop 208 prevents longitudinal movement of stent-graft 100 as outer sleeve 210 is retracted or otherwise removed to release stent-graft 100. Stop 208 includes a lumen 209 through which stent capture tube 284 and inner tube 205 are disposed. Stop 208 further includes grooves 214 disposed between landings 215. Stop 208 in this embodiment extends proximally along the length of the delivery system 200. Side tube 224 may be disposed in any of the grooves 214 and extend proximally the length of the delivery system to be control at proximal portion 250 through side lumen access 264. Stent-graft 100 is disposed within outer sleeve 210 in a compressed or delivery configuration wherein the diameter of stent-graft 100 is reduced such that it can be inserted through the vasculature.

Second guide wire 222 extends through stent-graft delivery system 200 through a lumen of side tube 224, which extends through lumen 116 of stent-graft 100, through lumen 130 of mobile external coupling 120, between outer sleeve 210 and body 107, and out a distal end of outer sleeve 210 through groove 218 of tip 202. In the delivery or compressed configuration, mobile external coupling 120 may be folded as shown schematically in FIGS. 18 and 19.

Stent capture system 290 is shown in FIG. 22. Stent capture system 290 includes a spindle 270 and a stent capture assembly 280. Stent capture system 290 may be similar to or identical to stent capture system described in U.S. Published Application Publication No. 2009/0276027, published Nov. 5, 2009, which is incorporated by reference herein in its entirety.

Figure 21:
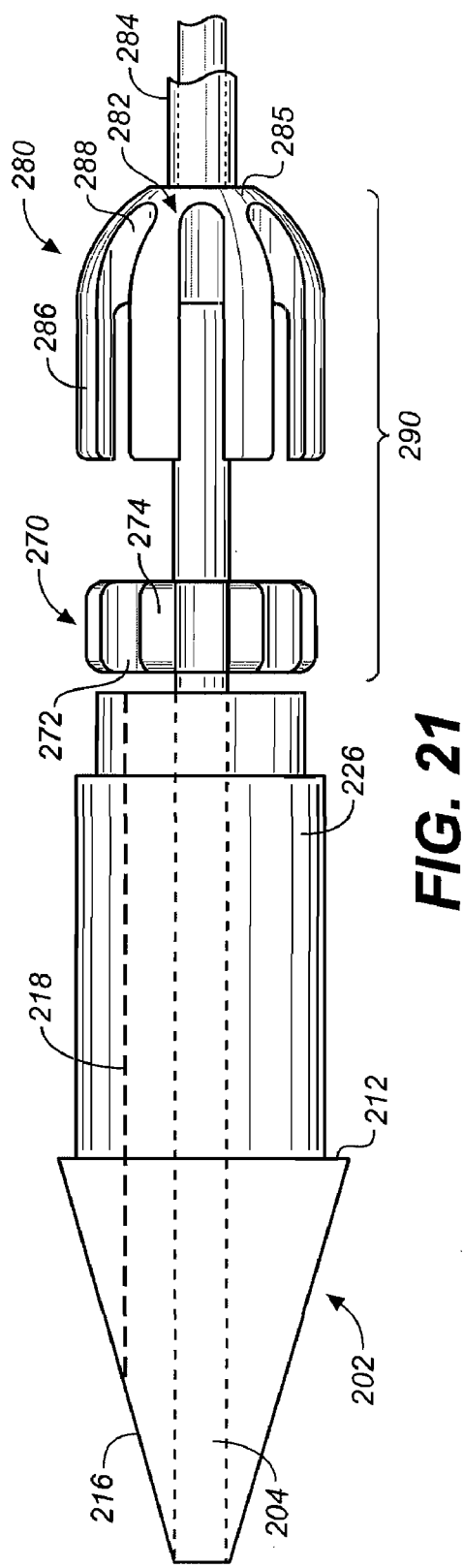
FIG. 21 is a schematic illustration of a stent capture assembly of the delivery system of FIG. 16.

Spindle 270 shown in FIG. 21 is fixed to inner shaft 205 adjacent a proximal end of tip 202. Spindle 270 includes a lumen (not shown) through which inner shaft is disposed. Spindle 270 may also be slidable relative to inner shaft 205, for example, as described in U.S. Published Application Publication No. 2009/0276027. Spindle 270 includes a number of spindle pins 274 disposed around the circumference of the spindle body. A spindle groove 272 is formed between each pair of adjacent spindle pins 274. A single stent crown (not shown) of proximal anchor stent 112 wraps around each spindle pin 274 and is held in place by a stent capture fitting arm 286 of the stent capture assembly 280 during stent-graft delivery. When the stent capture assembly 280 is retracted, the stent crowns are freed from the spindle pins 274 and proximal anchor stent 112 expands into position in the vessel. The spindle 270 can be made of any rigid and/or compliant biocompatible material and can be formed as a single unit and/or assembled from individual parts. Those skilled in the art will appreciate that the spindle 270 can made of any biocompatible material and can be formed as a single unit and/or assembled from individual parts. Other embodiments of spindle 270, as described for example in U.S. Published Application Publication No. 2009/0276027, may also be used.

Stent capture assembly 280 includes a stent capture fitting 282 and a stent capture shaft 284. The stent capture assembly 280 defines a stent capture assembly lumen (not shown) along its length through which inner shaft 205 can slide. The diameter of the stent capture assembly lumen is large enough that the inner shaft can slide within the stent capture assembly lumen. The stent capture shaft 284 advances the stent capture fitting 282 to hold the stent crowns wrapped around spindle pins 274 in place during delivery and initial deployment of stent-graft 100. Stent capture shaft 284 retracts the stent capture fitting 282 to release the proximal anchor stent 112 of the stent-graft 100 from the delivery diameter. The stent capture shaft 284 is long enough the reach through the vasculature from the stent graft deployment site in the vessel to the clinician. The proximal end of the stent capture shaft 284 is attached to stent capture slider 268 shown in FIGS. 16 and 17 for manipulation by the clinician during stent-graft delivery. Those skilled in the art will appreciate that the stent capture assembly 280 can made of any biocompatible material and can be formed as a single unit and/or assembled from individual parts. The stent capture shaft 284 may be constructed of a rigid plastic, such as PEEK polyetheretherketone, polyimide, nylon, or the like. The stent capture shaft 284 can alternatively be constructed of a flexible metal tube such as nitinol, stainless steel, or the like.

The stent capture fitting 282 in cooperation with the spindle 270, retains one end of the stent-graft during stent-graft delivery. In the illustrated embodiment, the stent capture fitting 282 includes a stent capture body 285 having a number of stent capture fitting arms 286 disposed around the circumference of the stent capture body 285. The stent capture body 285 defines a number of stent capture grooves 288 between each of the stent capture fitting arms 286 to receive the bare stent crowns. The stent capture fitting arms 286 can be substantially parallel to the central axis of the stent capture fitting 282, i.e., the axis along the stent capture shaft 284. In other embodiments, the stent capture fitting arms 286 can curve toward or away from the axis of the stent capture fitting 282 as desired for a particular purpose. When the stent capture fitting 282 is retracted, the stent capture fitting arms 286 release the bare stent crowns, and the proximal anchor stent 112 expands into position in the vessel. The stent capture fitting 282 can be made of any rigid and/or compliant biocompatible material and can be formed as a single unit and/or assembled from individual parts. The stent capture fitting may be fabricated from a variety of materials. This may include rigid plastic materials such as PEEK polyetheretherketone, polycarbonate, or the like, and may also include metals such as stainless steel. In one embodiment, a hard plastic or highly polished metal is desirable for the stent capture fitting 282 to avoid damage to the stent surface which is in contact with the stent capture fitting 282. The stent capture fitting 282 can be fastened to the stent capture shaft 284 by bonding the two with adhesive or threading the two components together. The stent capture fitting 282 may alternatively be insert molded directly on the stent capture shaft 284.

Figure 23:
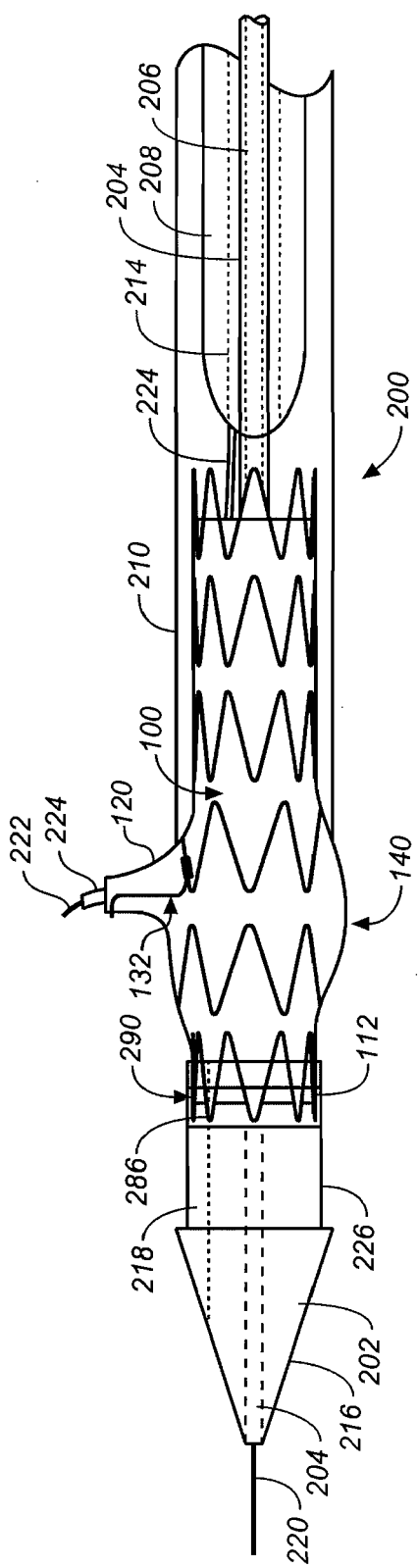
FIGS. 23-26 are schematic illustrations of progressive steps of deploying the stent-graft from the delivery system of FIG. 16.

Outer sleeve 210 is a hollow tube and defines a lumen therein within which stent-graft 100, stent capture system 290, side shaft 224 and inner tube 205 are disposed in the delivery configuration shown in FIG. 18. In a first step for deploying the stent-graft, outer sleeve 210 is moved proximally, retracted, relative to inner tube 205 to a position adjacent the mobile external coupling 120, as shown in FIG. 23.

Figure 23A:
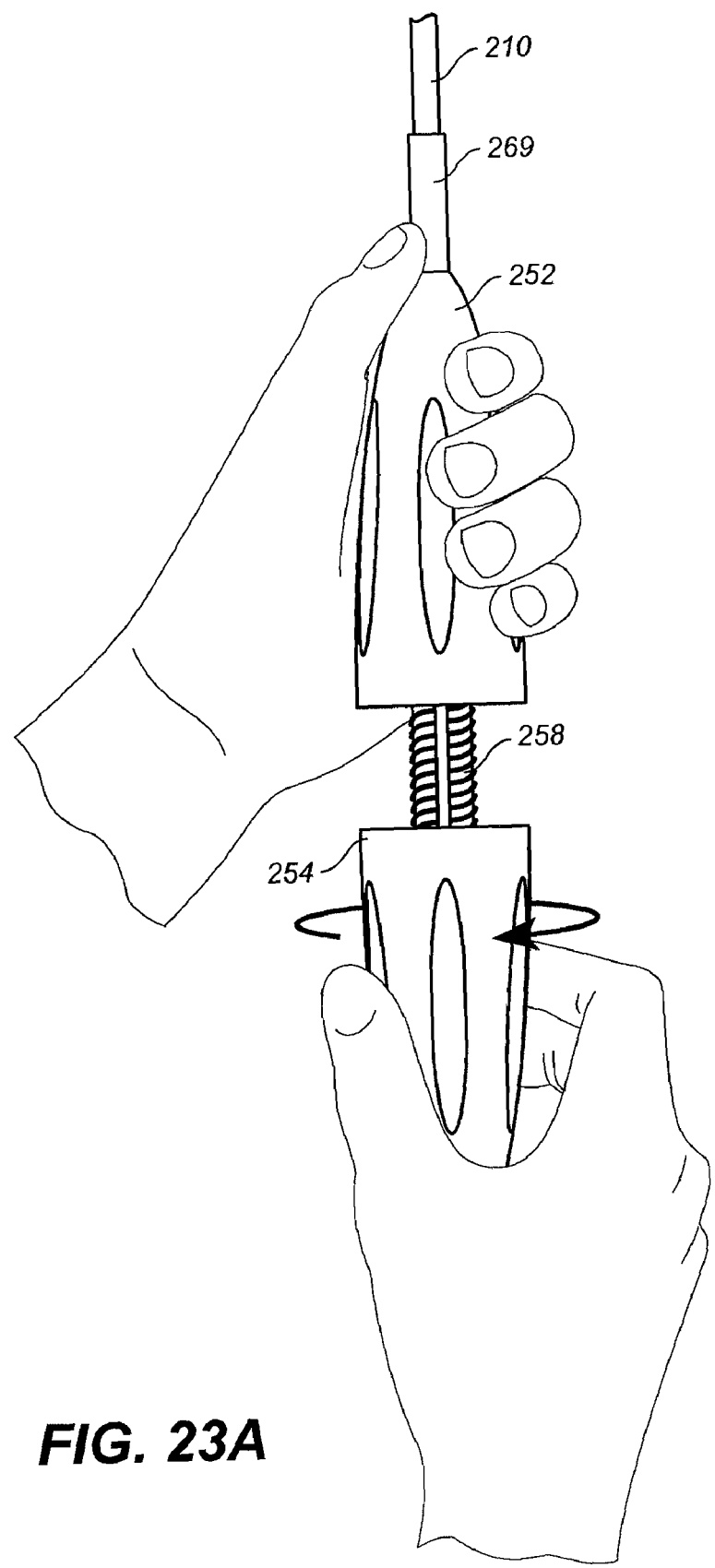

Outer sleeve 210 may be refracted by retracting external slider 254 by counter-clockwise rotational movement, as shown in FIG. 23A. This rotational movement provides a slower retraction of outer sleeve 210 a controlled release of the proximal portion of stent-graft 100, as shown in FIG. 23. Due to stent capture assembly 290 holding proximal anchor stent 112 of the stent-graft 100 in the radially compressed delivery configuration, and the relatively short distance to the mobile external coupling 120, the portion 190 of the stent that is free to expand is relatively short, as shown in FIG. 23. However, as also shown in FIG. 23, mobile external coupling 120 is no longer constrained by outer sleeve 210, and the energy stored in coupling deployment device 132 is released such that mobile external coupling 120 pops-out from body 107 and into the ostium of the branch vessel.

The side tube 224 may be removed by withdrawing it proximally from side lumen access 264 at the proximal portion 250 of the delivery system 200. Second guide wire 222 may be manipulated to adjust the location or orientation of mobile external coupling 120. Optionally, side tube 224 may remain in place while mobile external coupling 120 is adjusted.

Figure 24:
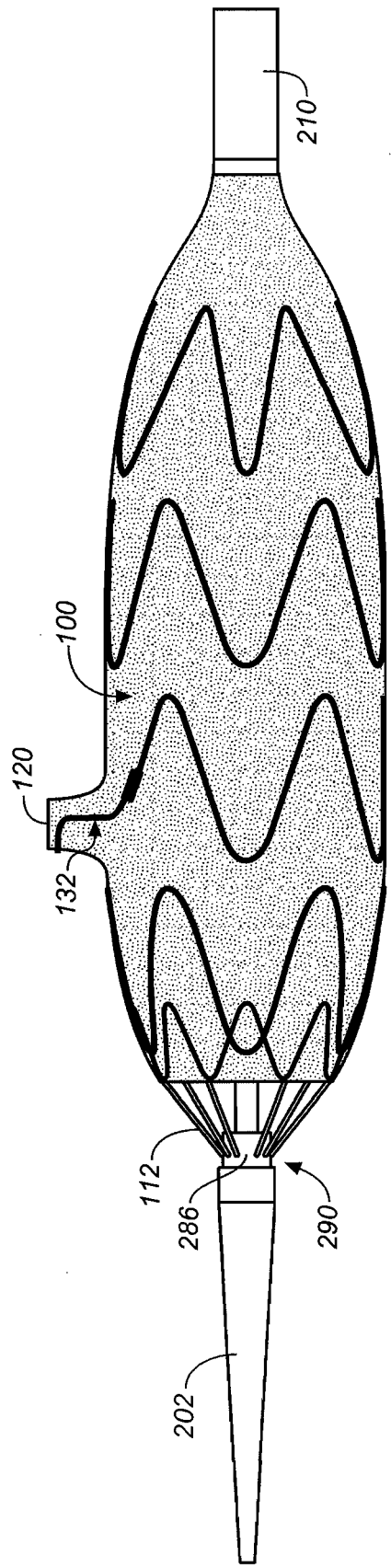
Figure 24A:
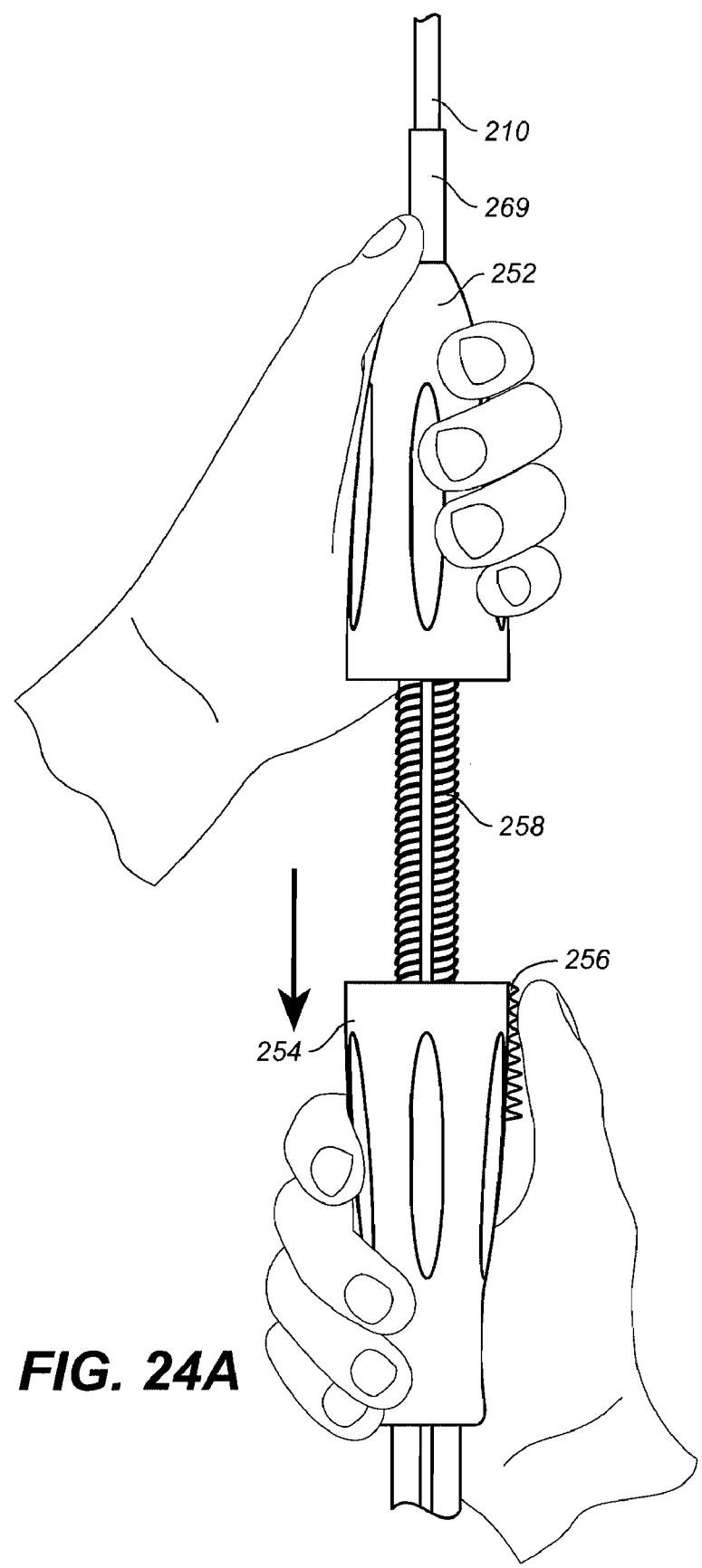
Figure 25:
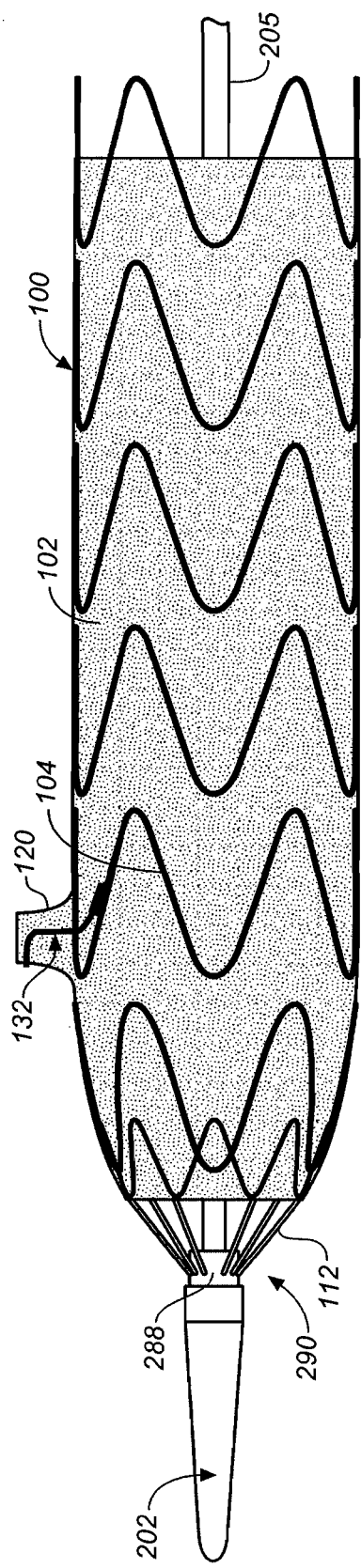

After mobile external coupling 120 is properly located in the ostium of the branch vessel, outer sleeve 210 may be further retracted, as shown in FIG. 24, by further retracting external slider 254. FIG. 24 shows outer sleeve 210 further retracted, but not fully retracted, as distal anchor stent 114 of stent-graft 100 remains disposed within outer sleeve 210. When outer sleeve 210 is fully retracted, as shown in FIG. 25, the entire stent-graft body, except for the portion retained by stent capture assembly 290, is in the radially expanded or deployed configuration. This further retraction of external slider 254 may be done more quickly than the initial controlled retraction by pressing trigger 256 and sliding external slider 254, as shown in FIG. 24A, rather than rotating external slider 254. However, those of ordinary skill in the art will recognize that the initial retraction and further retraction of external slider 254 may each be accomplished through rotation of external slider 254 or sliding of external slider 254. Further, other methods and devices for retracting outer sleeve 210 could be utilized, as known to those of ordinary skill in the art.

Figure 26:
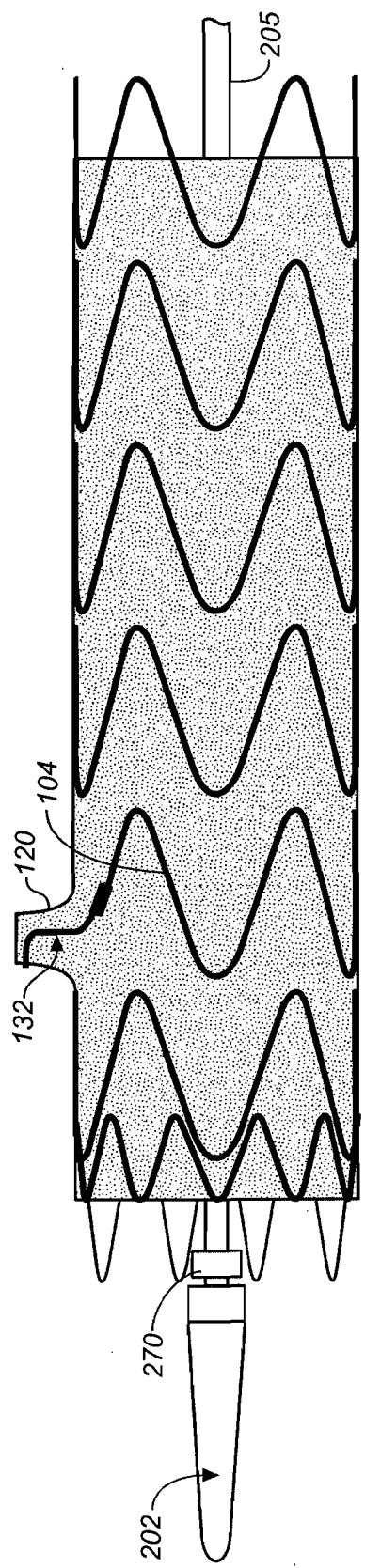

After outer sleeve 210 is fully retracted, stent capture slider 268 may be retracted proximally such that stent capture assembly 280 moves proximally away from spindle 270. Stent capture fitting arms 288 thereby release proximal anchor stent 112 such that proximal anchor stent expands, as shown in FIG. 26.

The stent-graft delivery system 200 described herein is only an example of a delivery system that can be used to delivery and deploy stent-graft 100 and many other delivery systems known to those skilled in the art could be utilized. For example, stent-graft 100 could be mounted onto a balloon to be expanded when at the target site. Other stent-graft-delivery systems, for example and not by way of limitation, the delivery systems described in U.S. Published Patent Application Publication Nos. 2008/0114442 and 2008/0262590 and U.S. Pat. No. 7,264,632, and U.S. patent application Ser. Nos. 12/425,616 and 12/425,628, each filed Apr. 17, 2009, each of which is incorporated herein by reference in its entirety, may be utilized to deliver and deploy stent-graft 100.

FIGS. 27-32 schematically show a method of delivering stent-graft 100 to a target site in a main vessel and a method of delivering a branch stent-graft to branch vessel. In the example described herein, the stent-graft 100 is delivered and deployed into the aorta 300. Portions of the aorta 300 include the ascending aorta 302, the aortic arch 304, and the descending aorta 306. Branching from the aortic arch are the brachiocephalic trunk 308, the left common carotid artery 314, and the left subclavian artery 316. The brachiocephalic trunk branches into the right subclavian artery 310 and the right common carotid artery 312. An aneurysm 318 in the area of the aortic arch 304 can be difficult to bypass or exclude with a stent-graft because blood flow to the branch arteries must be maintained.

In the embodiment shown in FIGS. 27-32, the aneurysm is sufficiently close to brachiocephalic trunk 308 that the stent-graft 100 must extend between the brachiocephalic trunk 308 and the heart. In such a case and with a stent-graft 100 with only a single mobile external coupling 120, the mobile external coupling 120 is designed so as to be deployed into the brachiocephalic trunk 308 to perfuse the brachiocephalic trunk 308. Prior to the procedure for inserting stent-graft 100, surgical by-pass procedures installing bypass grafts or vessels (not shown) are performed to connect the right common carotid artery 312 to the left common carotid artery 314 and the left common carotid artery to the left subclavian artery 316. Such surgical bypass procedures may be performed one to two weeks prior to insertion of the stent-graft, and present significantly less complications and risk than a surgical solution to repair an aneurysm 318 in the aortic arch. In this manner, maintaining perfusion to the brachiocephalic trunk 308, and hence the right common carotid artery 312, maintains perfusion to the left common carotid artery 314 and the left subclavian artery 316 Thus, the openings (or ostia) to these branch vessels directly from the aortic arch may be blocked by stent-graft 100. In the alternative, multiple mobile external couplings 120 may be provided in stent-graft 100. Further, if the aneurysm only affects the left common carotid artery 314 and the left subclavian artery 316, only one by-pass between the left common carotid artery 314 and the left subclavian artery needs to be performed, and then a stent-graft with a single mobile external coupling 120 can be utilized to perfuse the left common carotid artery 314. Alternatively, in such a situation, a stent-graft with two mobile external couplings may be provided, one for each of the branch vessels noted. Accordingly, while the embodiment of stent-graft 100 in the method described below includes a single mobile external coupling 120 and the mobile external coupling is deployed in the brachiocephalic trunk 308, those skilled in the art would recognize that multiple mobile external couplings can be used and the mobile external coupling(s) may be deployed in other branch arteries.

Figure 27:
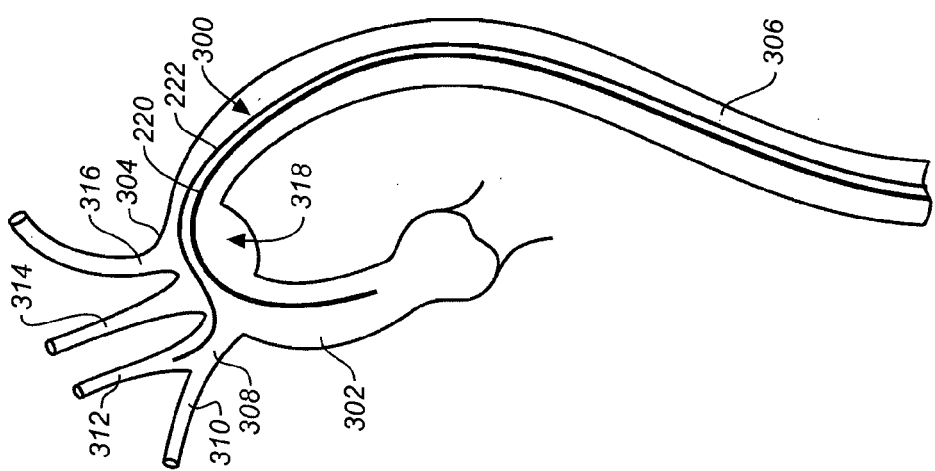

FIG. 27 shows the first guide wire 220 advanced through the descending aorta 306, through the aortic arch 304, and into the ascending aorta 302 and second guide wire 222 advanced through the descending aorta 306, through the aortic arch 304, and into brachiocephalic trunk 308. Guide wires 200, 222 are typically inserted into the femoral artery and routed up through the abdominal aorta, and into the thoracic aorta, as is known in the art. Second guide wire 222 may also be locked at its distal end so as to prevent second guide wire 222 from retracting. Access from the brachiocephalic artery or carotid artery may be used to lock second guide wire 222 at its distal or superaortic end, as is known to those of ordinary skill in the art as a through-and-through wire technique.

Figure 28:
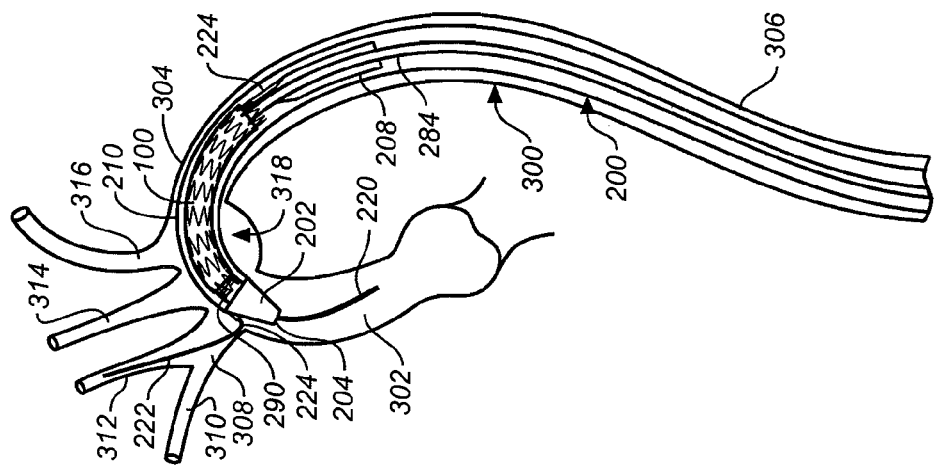

FIG. 28 shows stent-graft delivery system 200, with stent-graft 100 compressed therein, advanced over guide wires 220, 222 to the target location in the aortic arch 304. The location of the stent-graft delivery system 200 and/or the stent-graft 100 may be verified radiographically and delivery system 200 and/or stent-graft 100 may include radiopaque markers as known in the art.

Figure 29:
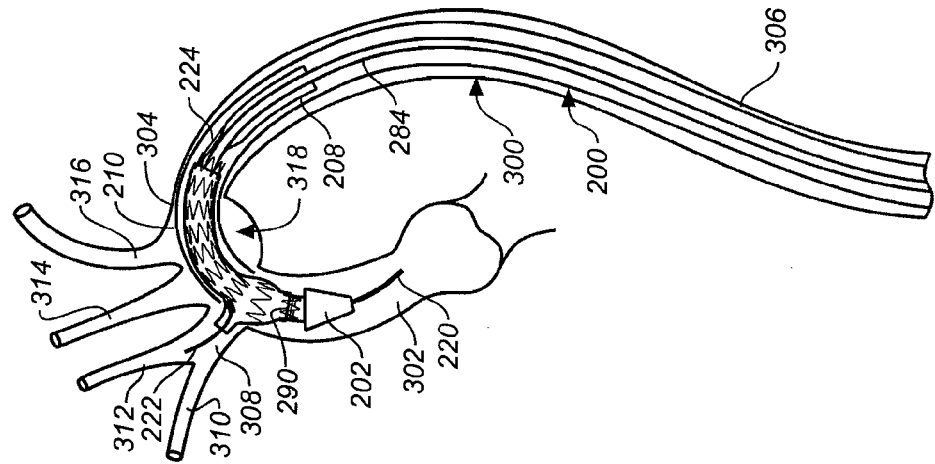
FIGS. 27-32 are schematic illustrations of progressive steps a method for delivering and deploying the stent-graft of FIG. 1 and a branch stent-graft to a target location

After stent-graft delivery system 200 is in the location where the mobile external coupling 120 of the stent graft 100 is approximately aligned with the opening into the branch vessel, outer sleeve 210 is retracted proximally to a position adjacent to mobile external coupling 120 to release mobile external coupling 120, as shown in FIG. 29 (also shown in FIG. 23). Mobile external coupling 120 provides a positive outward force due to coupling deployment device 132 that reduces the possibility of the mobile external coupling 120 collapsing against or within body 107 after deployment. Delivery system 200 may then be moved and/or rotated to better align mobile external coupling 120 with the branch artery, in this case, the brachiocephalic trunk 308. Further, due to the configuration of mobile external coupling 120, even if it is not perfectly aligned with brachiocephalic trunk 308, the top of the mobile external coupling 120 may be moved to properly align its lumen opening with the lumen of the brachiocephalic trunk 308 without having to move the entire stent-graft 100. Force to adjust the position of the top of the mobile external coupling 120 can be created by pulling or pushing on the end of second guide wire 222. Coupling deployment device 132, as explained above, urges the distal end of mobile external coupling 120 distally away from the main graft and into the lumen of the branch vessel.

Figure 30:
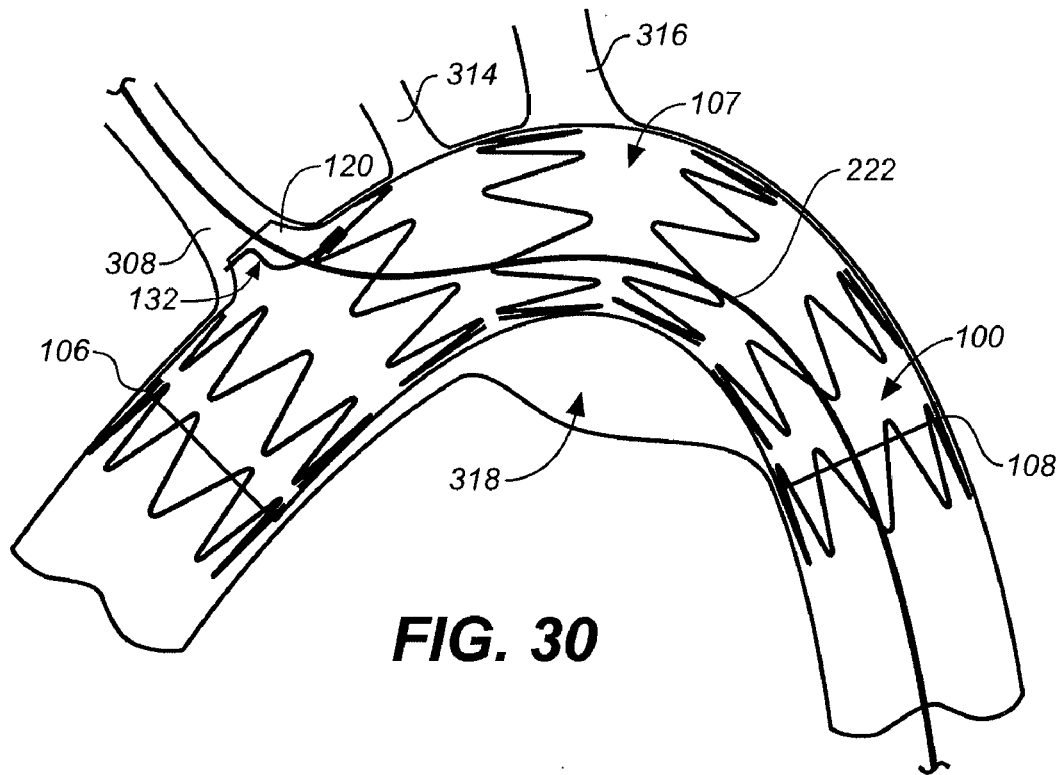
Figure 31:
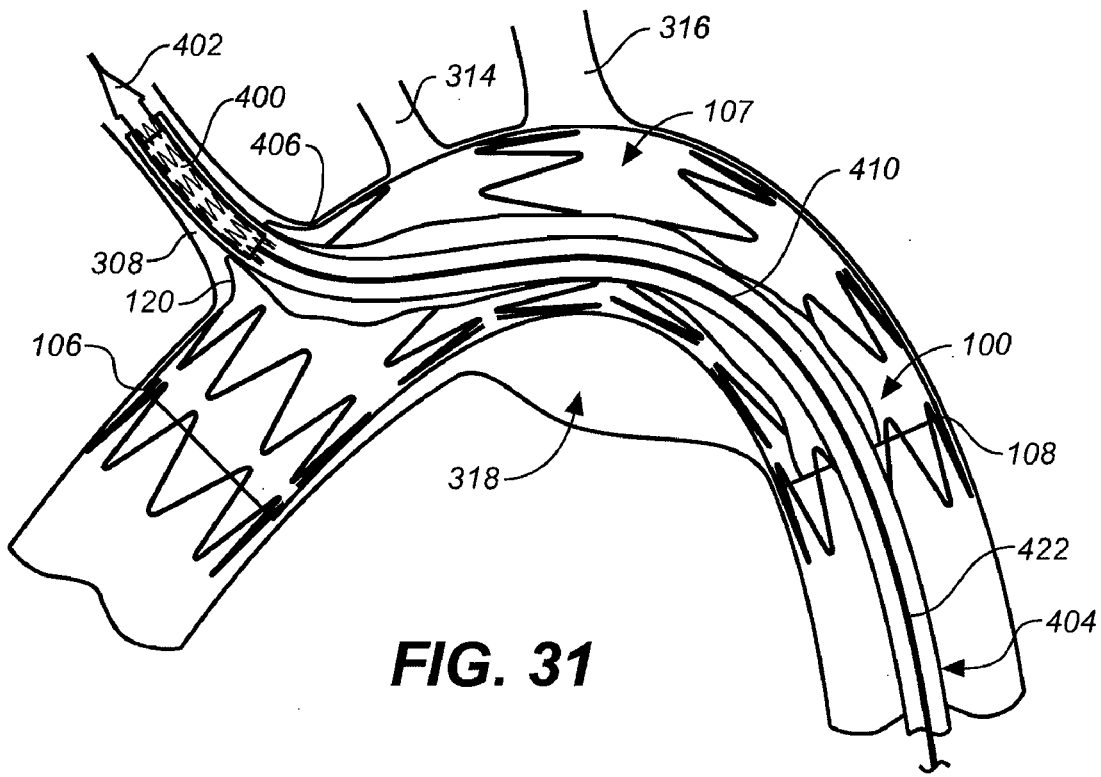
Figure 32:
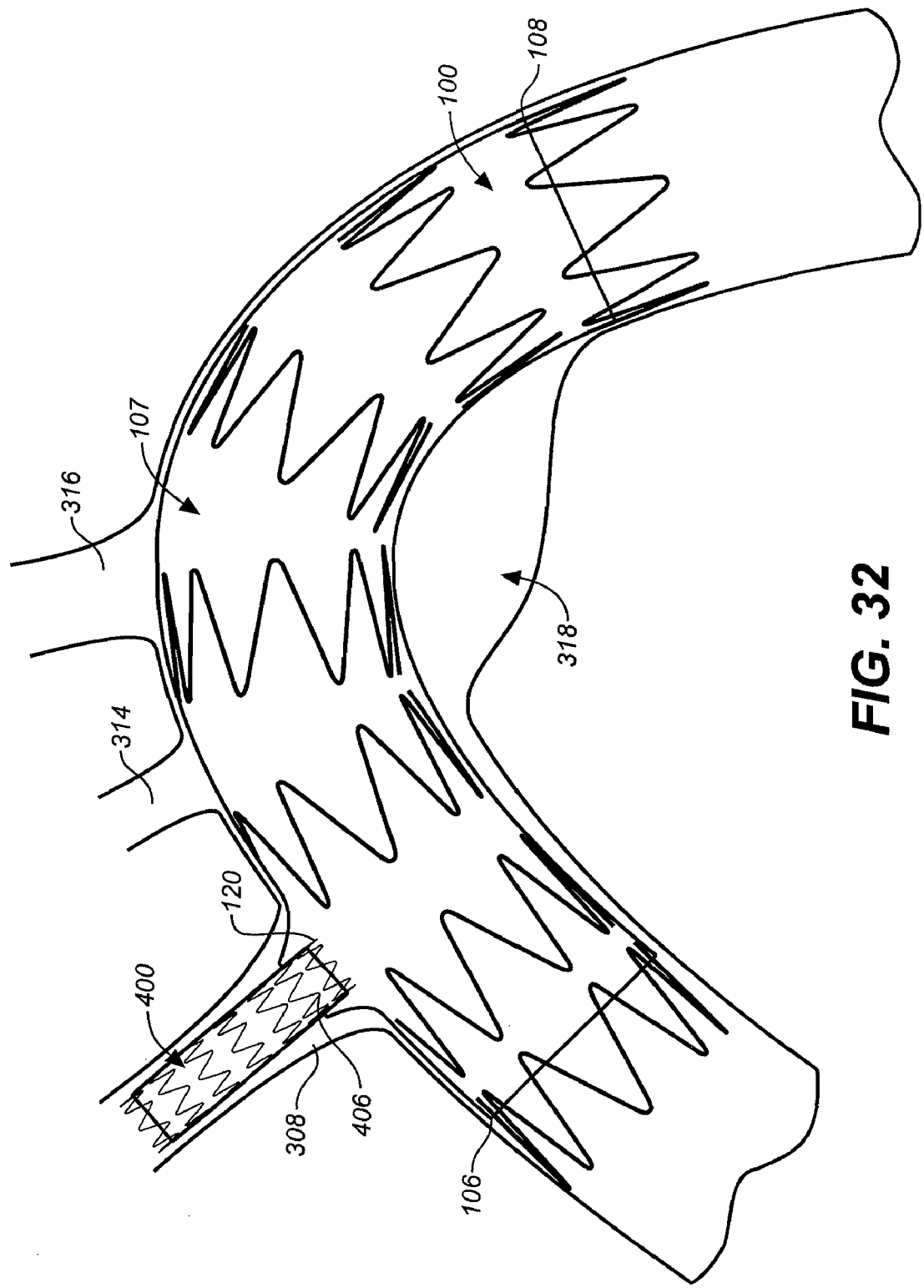

Once mobile external coupling 120 is deployed and in position in the brachiocephalic trunk 308, outer sleeve 210 may be further retracted as explained above with respect to FIGS. 24, 25 and 24A, thereby deploying the main body of the stent graft 100, as shown in FIGS. 24 and 25. The stent capture fitting 282 is then retracted proximally to release proximal anchor stent 112 of stent 100 to fully release stent-graft 100, as shown in FIGS. 26 and 30. Once mobile external coupling 120 and stent-graft 100 are deployed, delivery system 200 may be removed. Second guide wire 222 may remain in place in brachiocephalic trunk 308 or may be replaced by another guide wire. A branch stent-graft delivery system 404 is advanced over second guide wire 222 and into brachiocephalic trunk 308, as shown in FIG. 31. Branch stent-graft delivery system includes a tip 402 and a sleeve (not shown), and contains therein a branch stent-graft 400. Branch stent-graft delivery system 404 and branch stent-graft 400 may be conventional. Branch stent-graft delivery system 404 is advanced into brachiocephalic trunk 308 such that a proximal portion 406 of branch stent-graft 400 remains inside of mobile external coupling 120. The sleeve constraining branch stent-graft 400 is then retracted proximally, thereby releasing branch stent-graft 400 from delivery system 404. The delivery system 404 is then withdrawn, as shown in FIG. 32. Proximal portion 406 of branch stent-graft 400 is disposed within internal sealing cuff 134 (obscured in FIG. 32) when branch stent-graft 400 is expanded.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. It will also be understood that each feature of each embodiment discussed herein, and of each reference cited herein, can be used in combination with the features of any other embodiment. All patents and publications discussed herein are incorporated by reference herein in their entirety.

What is claimed is:

1. An endovascular prosthesis having a radially collapsed configuration and a radially expanded configuration comprising:

a tubular body having a proximal end, a distal end, and a lumen disposed between the proximal and distal ends, the tubular body including a body graft material and a plurality of stents coupled to the body graft material;

a mobile external coupling extending outwardly from the tubular body in the radially expanded configuration, wherein the mobile external coupling is generally frustoconically shaped and includes a base coupled to the tubular body, a top spaced from the tubular body, and a coupling lumen disposed between the base and the top, wherein the coupling lumen is in flow communication with the body lumen and wherein the mobile external coupling includes a coupling graft material; and a sealing cuff attached to the top of the mobile external coupling in the radially collapsed configuration and the radially expanded configuration, the sealing cuff extending from the top of the mobile external coupling towards the tubular body within the coupling lumen in the radially expanded configuration, wherein the sealing cuff is formed from a graft material and is generally cylindrically shaped.

2. The prosthesis of claim 1, wherein the sealing cuff is a seamless woven tube of PET cloth.

3. The prosthesis of claim 1, wherein the sealing cuff is reinforced with a circumferential stent coupled thereto.

4. The prosthesis of claim 3, wherein the circumferential stent is formed from a shape memory material and formed into a sinusoidal configuration.

5. The prosthesis of claim 3, wherein the circumferential stent has a shape memory diameter that is at least 20% less than a diameter of the sealing cuff.

6. A main prosthesis and a branch vessel prosthesis assembly comprising:

a main prosthesis configured for placement in a main vessel, the main prosthesis having a main prosthesis radially compressed configuration and a main prosthesis radially expanded configuration, the main prosthesis including a tubular body and a mobile external coupling, the tubular body having a proximal end, a distal end, a body lumen disposed between the proximal and distal ends, and a body graft material, the mobile external coupling extending outwardly from the tubular body in the main prosthesis radially expanded configuration, and the mobile external coupling including a generally frustoconically shaped coupling graft material and including a coupling lumen in flow communication with the body lumen, wherein the mobile external coupling includes a base coupled to the tubular body and a top spaced from the tubular body;

a branch vessel prosthesis configured for placement in a branch vessel that extends from the main vessel, the branch prosthesis having a branch prosthesis radially compressed configuration and a branch prosthesis radially expanded configuration, the branch vessel prosthesis including an outer surface; and a cylindrical sealing cuff attached to the top of the mobile external coupling in the main prosthesis radially compressed configuration and the main prosthesis radially expanded configuration, the sealing cuff extending from the top of the mobile external coupling towards the tubular body within the coupling lumen in the main prosthesis radially expanded configuration, wherein the sealing cuff overlaps a proximal portion of the branch vessel prosthesis such that the outer surface of the branch vessel prosthesis contacts an inner surface of the sealing cuff in the main prosthesis radially expanded configuration and the branch prosthesis radially expanded configuration.

7. The prosthesis of claim 6, wherein a diameter of the sealing cuff in the main prosthesis radially expanded configuration is smaller than a diameter of a portion of the branch vessel prosthesis that is not disposed within the sealing cuff in the branch prosthesis radially expanded configuration.

8. The prosthesis of claim 7, wherein the diameter of the sealing cuff is up to 30% smaller than the diameter of the portion of the branch vessel prosthesis that is not disposed within the sealing cuff.

9. The prosthesis of claim 6, wherein the sealing cuff is a seamless woven tube of PET cloth.

10. The prosthesis of claim 6, wherein the sealing cuff is reinforced with a circumferential stent coupled thereto.

11. The prosthesis of claim 10, wherein the circumferential stent is formed from a shape memory material and formed into a sinusoidal configuration.

12. The prosthesis of claim 10, wherein the circumferential stent has a shape memory diameter that is at least 20% less than a diameter of the sealing cuff.

* * * * *